United States Patent
Sarrafzadeh et al.

(10) Patent No.: US 11,779,265 B2
(45) Date of Patent: Oct. 10, 2023

(54) SEM SCANNER SENSING APPARATUS, SYSTEM AND METHODOLOGY FOR EARLY DETECTION OF ULCERS

(71) Applicants: BRUIN BIOMETRICS, LLC, Los Angeles, CA (US); THE REGENTS OF THE UNIVERSITY OF CALIFORNIA, Oakland, CA (US)

(72) Inventors: Majid Sarrafzadeh, Anaheim Hills, CA (US); William Kaiser, Los Angeles, CA (US); Alireza Mehrnia, Los Angeles, CA (US); Barbara M. Bates-Jensen, Pasadena, CA (US); Frank Wang, Cupertino, CA (US); Michael Flesch, Beverly Hills, CA (US); Joseph Boystak, Marina Del Rey, CA (US); Yeung Lam, Sherman Oaks, CA (US)

(73) Assignees: Bruin Biometrics, LLC, Los Angeles, CA (US); The Regents of the University of California, Oakland, CA (US)

( * ) Notice: Subject to any disclaimer, the term of this patent is extended or adjusted under 35 U.S.C. 154(b) by 1126 days.

(21) Appl. No.: 16/440,687

(22) Filed: Jun. 13, 2019

(65) Prior Publication Data
US 2019/0290189 A1 Sep. 26, 2019

Related U.S. Application Data

(63) Continuation of application No. 16/210,911, filed on Dec. 5, 2018, now Pat. No. 11,253,192, which is a (Continued)

(51) Int. Cl.
*A61B 5/00* (2006.01)
*A61B 5/05* (2021.01)
(Continued)

(52) U.S. Cl.
CPC ............ *A61B 5/447* (2013.01); *A61B 5/05* (2013.01); *A61B 5/0533* (2013.01);
(Continued)

(58) Field of Classification Search
CPC ......... A61B 5/447; A61B 5/05; A61B 5/0533; A61B 5/0537; A61B 5/443; A61B 5/445;
(Continued)

(56) References Cited

U.S. PATENT DOCUMENTS 3,851,641 A  12/1974 Toole et al.
4,295,009 A  10/1981 Weidler
(Continued)

FOREIGN PATENT DOCUMENTS

AU  2020103438 A4  1/2021
CA  2811609  11/2011
(Continued)

OTHER PUBLICATIONS

Bates-Jensen et al., Subepidermal moisture differentiates erythema and stage I pressure ulcers in nursing home residents, Wound Repair and Regeneration, vol. 16, #2, pp. 189-197 (Year: 2008).*
(Continued)

*Primary Examiner* — Jacqueline Cheng
*Assistant Examiner* — Tho Q Tran
(74) *Attorney, Agent, or Firm* — Arnold & Porter Kaye Scholer LLP

(57) ABSTRACT

A handheld, conforming capacitive sensing apparatus configured to measure Sub-Epidermal Moisture (SEM) as a mean to detect and monitor the formation of pressure ulcers. The device incorporates an array of electrodes which are excited to measure and scan SEM in a programmable and multiplexed manner by a battery-less RF-powered chip. The scanning operation is initiated by an interrogator which excites a coil embedded in the apparatus and provides the
(Continued)

needed energy burst to support the scanning/reading operation. Each electrode measures the equivalent sub-epidermal capacitance corresponding and representing the moisture content.

16 Claims, 18 Drawing Sheets

Related U.S. Application Data continuation of application No. 15/095,046, filed on Apr. 9, 2016, now Pat. No. 10,188,340, which is a continuation of application No. 15/058,964, filed on Mar. 2, 2016, now Pat. No. 9,980,673, which is a continuation of application No. 14/827,375, filed on Aug. 17, 2015, now Pat. No. 9,398,879, which is a continuation of application No. 14/297,977, filed on Jun. 6, 2014, now Pat. No. 9,220,455, which is a continuation of application No. 13/668,047, filed on Nov. 2, 2012, now abandoned, which is a continuation of application No. PCT/US2011/035618, filed on May 6, 2011.

(60) Provisional application No. 61/453,852, filed on Mar. 17, 2011, provisional application No. 61/332,755, filed on May 8, 2010.

(51) Int. Cl.
*A61B 5/0533* (2021.01)
*A61B 5/0537* (2021.01)

(52) U.S. Cl.
CPC ............ *A61B 5/0537* (2013.01); *A61B 5/443* (2013.01); *A61B 5/445* (2013.01); *A61B 5/6843* (2013.01); *A61B 5/6844* (2013.01); *A61B 5/7271* (2013.01); *A61B 5/7285* (2013.01); *A61B 2562/0214* (2013.01); *A61B 2562/0247* (2013.01); *A61B 2562/04* (2013.01); *A61B 2562/046* (2013.01); *A61B 2562/066* (2013.01); *A61B 2562/164* (2013.01)

(58) Field of Classification Search
CPC ... A61B 5/6843; A61B 5/6844; A61B 5/7271; A61B 5/7285; A61B 2562/0214; A61B 2562/0247; A61B 2562/04; A61B 2562/046; A61B 2562/066; A61B 2562/164

See application file for complete search history.

(56) References Cited

U.S. PATENT DOCUMENTS

| | | | |
|---|---|---|---|
| 4,557,271 A | 12/1985 | Stoller et al. | |
| 4,857,716 A | 8/1989 | Gombrich et al. | |
| 4,860,753 A * | 8/1989 | Amerena | A61B 5/442 324/690 |
| 5,001,436 A * | 3/1991 | Scot | A61B 5/442 324/692 |
| 5,073,126 A | 12/1991 | Kikuchi et al. | |
| 5,284,150 A | 2/1994 | Butterfield et al. | |
| 5,292,341 A | 3/1994 | Snell | |
| 5,367,789 A | 11/1994 | Lamont | |
| 5,815,416 A | 9/1998 | Liebmann et al. | |
| 5,904,581 A | 5/1999 | Pope et al. | |
| 6,223,088 B1 | 4/2001 | Scharnberg et al. | |
| 6,312,263 B1 | 11/2001 | Higuchi et al. | |
| 6,330,479 B1 | 12/2001 | Stauffer | |
| 6,368,284 B1 | 4/2002 | Bardy | |
| 6,370,426 B1 | 4/2002 | Campbell et al. | |
| 6,434,422 B1 | 8/2002 | Tomoda et al. | |
| 6,577,700 B1 | 6/2003 | Fan et al. | |
| 6,634,045 B1 | 10/2003 | DuDonis et al. | |
| 6,738,798 B1 | 5/2004 | Ploetz et al. | |
| 6,756,793 B2 | 6/2004 | Hirono et al. | |
| 6,963,772 B2 | 11/2005 | Bloom et al. | |
| 7,079,899 B2 | 7/2006 | Petrofsky | |
| 7,315,767 B2 | 1/2008 | Caduff et al. | |
| 7,402,135 B2 | 7/2008 | Leveque et al. | |
| 7,783,344 B2 | 8/2010 | Lackey et al. | |
| 8,011,041 B2 | 9/2011 | Hann | |
| 8,060,315 B2 | 11/2011 | Brosette et al. | |
| 8,355,925 B2 | 1/2013 | Rothman et al. | |
| 8,390,583 B2 | 3/2013 | Forutanpour et al. | |
| 8,494,617 B2 | 7/2013 | Baker, Jr. et al. | |
| 8,648,707 B2 | 2/2014 | Franz et al. | |
| 8,690,785 B2 * | 4/2014 | Lading | A61B 5/02125 600/481 |
| 8,925,392 B2 | 1/2015 | Esposito et al. | |
| 9,028,407 B1 | 5/2015 | Bennett-Guerrero | |
| 9,095,305 B2 | 8/2015 | Engler et al. | |
| 9,220,455 B2 | 12/2015 | Sarrafzadeh et al. | |
| 9,271,676 B2 | 3/2016 | Alanen et al. | |
| 9,398,879 B2 | 7/2016 | Sarrafzadeh et al. | |
| 9,675,289 B2 | 6/2017 | Heaton | |
| 9,763,596 B2 | 9/2017 | Tonar et al. | |
| 9,949,683 B2 | 4/2018 | Afentakis | |
| 9,980,673 B2 | 5/2018 | Sarrafzadeh et al. | |
| 10,085,643 B2 | 10/2018 | Bandic et al. | |
| 10,166,387 B2 | 1/2019 | Bergelin et al. | |
| 10,178,961 B2 | 1/2019 | Tonar et al. | |
| 10,182,740 B2 | 1/2019 | Tonar et al. | |
| 10,188,340 B2 | 1/2019 | Sarrafzadeh et al. | |
| 10,194,856 B2 | 2/2019 | Afentakis et al. | |
| 10,206,604 B2 | 2/2019 | Bergelin et al. | |
| 10,226,187 B2 | 3/2019 | Al-Ali et al. | |
| 10,278,636 B2 | 5/2019 | Wu et al. | |
| 10,285,898 B2 | 5/2019 | Douglas et al. | |
| 10,307,060 B2 | 6/2019 | Tran | |
| 10,342,482 B1 | 7/2019 | Lisy et al. | |
| 10,383,527 B2 | 8/2019 | Al-Ali | |
| 10,420,602 B2 | 9/2019 | Horton et al. | |
| 10,441,185 B2 | 10/2019 | Rogers et al. | |
| 10,448,844 B2 | 10/2019 | Al-Ali et al. | |
| 10,463,293 B2 | 11/2019 | Maharbiz et al. | |
| 10,485,447 B2 | 11/2019 | Tonar et al. | |
| 10,898,129 B2 | 1/2021 | Burns et al. | |
| 10,950,960 B2 | 3/2021 | Burns et al. | |
| 11,191,477 B2 | 12/2021 | Burns | |
| 11,253,192 B2 | 2/2022 | Sarrafzadeh et al. | |
| 11,284,810 B2 | 3/2022 | Tonar et al. | |
| 11,304,652 B2 | 4/2022 | Burns et al. | |
| 11,337,651 B2 | 5/2022 | Burns et al. | |
| 11,342,696 B2 | 5/2022 | Burns et al. | |
| 11,426,118 B2 | 8/2022 | Burns | |
| 11,534,077 B2 | 12/2022 | Tonar et al. | |
| 2001/0051783 A1 | 12/2001 | Edwards et al. | |
| 2002/0016535 A1 | 2/2002 | Martin et al. | |
| 2002/0070866 A1 | 6/2002 | Newham | |
| 2002/0112898 A1 | 8/2002 | Honda et al. | |
| 2002/0143262 A1 | 10/2002 | Bardy | |
| 2003/0009244 A1 | 1/2003 | Engleson et al. | |
| 2003/0036674 A1 | 2/2003 | Bouton | |
| 2003/0036713 A1 | 2/2003 | Bouton et al. | |
| 2003/0110662 A1 | 6/2003 | Gilman et al. | |
| 2003/0116447 A1 | 6/2003 | Surridge et al. | |
| 2003/0139255 A1 | 7/2003 | Lina | |
| 2004/0041029 A1 | 3/2004 | Postman et al. | |
| 2004/0046668 A1 | 3/2004 | Smith et al. | |
| 2004/0054298 A1 | 3/2004 | Masuo et al. | |
| 2004/0080325 A1 | 4/2004 | Ogura | |
| 2004/0133092 A1 | 7/2004 | Kain | |
| 2004/0147977 A1 | 7/2004 | Petrofsky | |
| 2004/0171962 A1 | 9/2004 | Leveque et al. | |
| 2004/0176754 A1 | 9/2004 | Island et al. | |
| 2004/0236200 A1 | 11/2004 | Say et al. | |
| 2004/0254457 A1 | 12/2004 | Van der Weide | |
| 2005/0027175 A1 | 2/2005 | Yang | |
| 2005/0070778 A1 | 3/2005 | Lackey et al. | |
| 2005/0086072 A1 | 4/2005 | Fox, Jr. et al. | |

(56) References Cited

U.S. PATENT DOCUMENTS

| | | |
|---|---|---|
| 2005/0096513 A1 | 5/2005 | Ozguz et al. |
| 2005/0177061 A1* | 8/2005 | Alanen .............. A61B 5/4878 600/547 |
| 2005/0203435 A1 | 9/2005 | Nakada |
| 2005/0215918 A1 | 9/2005 | Frantz et al. |
| 2005/0245795 A1 | 11/2005 | Goode et al. |
| 2005/0251418 A1 | 11/2005 | Fox, Jr. et al. |
| 2006/0052678 A1 | 3/2006 | Drinan et al. |
| 2006/0058593 A1 | 3/2006 | Drinan et al. |
| 2006/0097949 A1 | 5/2006 | Luebke et al. |
| 2006/0206013 A1 | 9/2006 | Rothman et al. |
| 2007/0043282 A1 | 2/2007 | Mannheimer et al. |
| 2007/0106172 A1 | 5/2007 | Abreu |
| 2007/0179585 A1 | 8/2007 | Chandler et al. |
| 2007/0191273 A1 | 8/2007 | Ambati et al. |
| 2007/0213700 A1 | 9/2007 | Davison et al. |
| 2007/0248542 A1 | 10/2007 | Kane et al. |
| 2008/0009764 A1 | 1/2008 | Davies |
| 2008/0015894 A1 | 1/2008 | Miller et al. |
| 2008/0039700 A1 | 2/2008 | Drinan et al. |
| 2008/0048680 A1 | 2/2008 | Hargreaves et al. |
| 2008/0259577 A1 | 10/2008 | Hu et al. |
| 2008/0278336 A1 | 11/2008 | Ortega et al. |
| 2009/0047694 A1 | 2/2009 | Shuber |
| 2009/0076410 A1 | 3/2009 | Libbus et al. |
| 2009/0104797 A1 | 4/2009 | Tseng et al. |
| 2009/0124924 A1 | 5/2009 | Eror et al. |
| 2009/0189092 A1 | 7/2009 | Aoi et al. |
| 2009/0209830 A1 | 8/2009 | Nagle et al. |
| 2009/0285785 A1 | 11/2009 | Jimi et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0113979 A1 | 5/2010 | Sarrafzadeh et al. |
| 2010/0268111 A1 | 10/2010 | Drinan et al. |
| 2010/0298687 A1 | 11/2010 | Yoo et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0046505 A1 | 2/2011 | Cornish et al. |
| 2011/0160548 A1 | 6/2011 | Forster |
| 2011/0175844 A1* | 7/2011 | Berggren .............. G06F 3/044 345/174 |
| 2011/0184264 A1 | 7/2011 | Galasso, Jr. et al. |
| 2011/0191122 A1 | 8/2011 | Kharraz Tavakol et al. |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1* | 2/2013 | Rogers .............. H05K 1/0283 600/386 |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0288397 A1 | 6/2014 | Sarrafzadeh et al. |
| 2014/0200486 A1 | 7/2014 | Bechtel et al. |
| 2014/0221792 A1 | 8/2014 | Miller et al. |
| 2014/0273025 A1 | 9/2014 | Hurskainen et al. |
| 2014/0275823 A1 | 9/2014 | Lane et al. |
| 2014/0298928 A1 | 10/2014 | Duesterhoft et al. |
| 2014/0316297 A1 | 10/2014 | McCaughan et al. |
| 2014/0318699 A1 | 10/2014 | Longinotti-Buitoni et al. |
| 2015/0002168 A1 | 1/2015 | Kao et al. |
| 2015/0009168 A1 | 1/2015 | Levesque et al. |
| 2015/0094548 A1 | 4/2015 | Sabatini et al. |
| 2015/0157435 A1 | 6/2015 | Chasins et al. |
| 2015/0186607 A1 | 7/2015 | Gileijnse et al. |
| 2015/0230863 A1 | 8/2015 | Youngquist et al. |
| 2015/0343173 A1 | 12/2015 | Tobescu et al. |
| 2015/0363567 A1 | 12/2015 | Pettus |
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0058342 A1 | 3/2016 | Maiz-Aguinaga et al. |
| 2016/0072308 A1 | 3/2016 | Nyberg et al. |
| 2016/0100790 A1 | 4/2016 | Cantu et al. |
| 2016/0101282 A1 | 4/2016 | Bergelin et al. |
| 2016/0174631 A1 | 6/2016 | Tong et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1 | 9/2016 | Larson et al. |
| 2016/0296268 A1 | 10/2016 | Gee et al. |
| 2016/0310034 A1 | 10/2016 | Tonar et al. |
| 2016/0338591 A1 | 11/2016 | Lachenbruch et al. |
| 2017/0007153 A1 | 1/2017 | Tonar et al. |
| 2017/0014044 A1 | 1/2017 | Tonar et al. |
| 2017/0014045 A1 | 1/2017 | Tonar et al. |
| 2017/0105646 A1* | 4/2017 | Bryenton ............. A61B 5/6824 |
| 2017/0156658 A1 | 6/2017 | Maharbiz et al. |
| 2017/0172489 A1 | 6/2017 | Afentakis |
| 2017/0188841 A1 | 7/2017 | Ma et al. |
| 2017/0238849 A1 | 8/2017 | Chapman et al. |
| 2017/0255812 A1 | 9/2017 | Kwon |
| 2017/0311807 A1 | 11/2017 | Fu et al. |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1 | 8/2018 | Burns et al. |
| 2018/0220953 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0053751 A1 | 2/2019 | Torres |
| 2019/0060602 A1 | 2/2019 | Tran et al. |
| 2019/0069836 A1 | 3/2019 | Hettrick |
| 2019/0104981 A1 | 4/2019 | Sarrafzadeh et al. |
| 2019/0104982 A1 | 4/2019 | Dunn et al. |
| 2019/0117964 A1 | 4/2019 | Bahrami et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0008299 A1 | 1/2020 | Tran et al. |
| 2020/0043607 A1 | 2/2020 | Zerhusen et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |

(56) References Cited

U.S. PATENT DOCUMENTS

| | | | |
|---|---|---|---|
| 2020/0296821 A1 | 9/2020 | Trublowski et al. | |
| 2020/0297244 A1 | 9/2020 | Brownhill et al. | |
| 2020/0297255 A1 | 9/2020 | Martinez et al. | |
| 2022/0287584 A1 | 9/2022 | Burns et al. | |

FOREIGN PATENT DOCUMENTS

| | | |
|---|---|---|
| CA | 2609842 C | 10/2016 |
| CN | 204119175 U | 1/2015 |
| CN | 104352230 A | 2/2015 |
| CN | 104567657 A | 4/2015 |
| CN | 105963074 A | 9/2016 |
| CN | 208111467 U | 11/2018 |
| DE | 102012011212 A1 | 12/2012 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2584808 A | 12/2020 |
| JP | 2001-178705 | 7/2001 |
| JP | 2003-169788 A | 6/2003 |
| JP | 2003-290166 A | 10/2003 |
| JP | 2005-52227 | 3/2005 |
| JP | 2009-268611 A | 11/2009 |
| JP | 4418419 | 2/2010 |
| JP | 2013-198639 A | 10/2013 |
| KR | 10-2014-0058445 | 5/2014 |
| WO | WO 96/10951 A1 | 4/1996 |
| WO | 2001/054580 A1 | 8/2001 |
| WO | WO 2002/080770 A1 | 10/2002 |
| WO | WO 2004/105602 A1 | 12/2004 |
| WO | WO 2006/029035 A1 | 3/2006 |
| WO | WO 2007/098762 A1 | 9/2007 |
| WO | 2009/144615 A1 | 12/2009 |
| WO | 2010/060102 A2 | 5/2010 |
| WO | 2011/004165 A1 | 1/2011 |
| WO | WO 2011/022418 A2 | 2/2011 |
| WO | 2011/080080 A1 | 7/2011 |
| WO | 2011/080262 A1 | 7/2011 |
| WO | 2011/091517 A1 | 8/2011 |
| WO | WO 2011/143071 A2 | 11/2011 |
| WO | 2013/116242 A2 | 8/2013 |
| WO | 2014/186894 A1 | 11/2014 |
| WO | 2015/003015 A2 | 1/2015 |
| WO | 2015/077838 A1 | 6/2015 |
| WO | 2015/168720 A1 | 11/2015 |
| WO | 2015/169911 A1 | 11/2015 |
| WO | WO 2015/195720 A1 | 12/2015 |
| WO | 2016/172264 A1 | 10/2016 |
| WO | WO 2016/172263 A1 | 10/2016 |
| WO | WO 2017/032393 A1 | 3/2017 |
| WO | 2017/218818 A2 | 12/2017 |
| WO | WO 2017/214188 A1 | 12/2017 |
| WO | 2018/071715 A1 | 4/2018 |
| WO | 2018/077560 A1 | 5/2018 |
| WO | 2018/115461 A1 | 6/2018 |
| WO | WO 2018/144938 | 8/2018 |
| WO | WO 2018/144941 | 8/2018 |
| WO | WO 2018/144943 | 8/2018 |
| WO | WO 2018/144946 | 8/2018 |
| WO | 2018/189265 A1 | 10/2018 |
| WO | 2018/209100 A1 | 11/2018 |
| WO | 2018/234443 A1 | 12/2018 |
| WO | WO 2018/236739 | 12/2018 |
| WO | WO 2019/020551 A1 | 1/2019 |
| WO | WO 2019/030384 A2 | 2/2019 |
| WO | WO 2019/048624 A1 | 3/2019 |
| WO | WO 2019/048626 A1 | 3/2019 |
| WO | WO 2019/048638 A1 | 3/2019 |
| WO | 2019/076967 A2 | 4/2019 |
| WO | WO 2019/072531 A1 | 4/2019 |
| WO | WO 2019/073389 A1 | 4/2019 |
| WO | 2019/096828 A1 | 5/2019 |
| WO | 2019/099810 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Alanen, "Measurement of Hydration in the Stratum Corneum with the MoistureMeter and Comparison with the Corneometer," *Skin Research and Technology*, 10:32-37 (2004).

Alberts et al., "The Extracellular Matrix of Animals," *Molecular Biology of the Cell*, 4th ed., pp. 1065-1127 (2002).

Allman et al., "Pressure Ulcer Risk Factors Among Hospitalized Patiens with Activity Limitation," *JAMA*, 273:865-870 (1995).

Anonymous, "Recommended Practices for Positioning the Patient in the Perioperative Practice Setting," in *Perioperative Standards, Recommended Practices, and Guidelines*, AORN, Inc., 525-548 (2006).

Arao et al., "Morphological Characteristics of the Dermal Papillae in the Development of Pressure Sores," *World Wide Wounds*, (1999).

Australian Intellectual Property Office, Office Action dated May 1, 2014 for corresponding Australian patent application No. 2011253253 (pp. 1-10) and pending claims (pp. 11-15) pp.1-15.

Australian Patent Office, Office Action dated Jun. 1, 2015, for corresponding Australian Patent Application No. 2011253253 (pp. 1-4) and claims (pp. 5-10) pp. 1-10.

Bader et al., "Effect of Externally Applied Skin Surface Forces on Tissue Vasculature," *Archives of Physical Medicine and Rehabilitation*, 67(11):807-11 (1986).

Barnes, "Moisture Meters for Use on Thin Lumber and Veneers," *Moisture Register Co.*, 1-5 (1956).

Bates-Jensen et al., "Subepidermal Moisture Predicts Erythema and Stage 1 Pressure Ulcers in Nursing Home Residents: A Pilot Study," *Journal of the American Geriatric Society*, 55:1199-1205 (2007).

Bates-Jensen et al., "Subepidermal moisture differentiates erythema and stage 1 pressure ulcers in nursing home residents," *Wound Repair Regeneration*, 16:189-197 (2008).

Bates-Jensen et al., "Subepidermal Moisture Is Associated With Early Pressure Ulcer Damage in Nursing Home Residents With Dark Skin Tones; Pilot Findings," *Journal of Wound Ostomy and Continence Nursing*, 36(3):277-284 (2009).

Bergstrand et al., "Pressure-induced Vasodilation and Reactive Hyperemia at Different Depths in Sacral Tissue Under Clinically Relevant Conditions," *Microcirculation*, 21:761-771 (2014).

Bergstrom et al., "Pressure Ulcers in Adults: Prediction and Prevention," *Clinical Practice Guideline—Quick Reference Guide for Clinicians*, 117 (1992).

Brem et al. "High cost of stage IV pressure ulcers," *American Journal of Surgery*, 200:473-477 (2010).

Brienza et al., "Friction-Induced Skin Injuries—Are They Pressure Ulcers?," *Journal of Wound Ostomy and Continence Nursing*, 42(1):62-64 (2015).

Carmo-Araujo et al., "Ischaemia and reperfusion effects on skeletal muscle tissue: morphological and histochemical studies," *International Journal of Experimental Pathology*, 88:147-154 (2007).

Ceelen et al., "Compression-induced damage and internal tissue strains are related," *Journal of Biomechanics*, 41:3399-3404 (2008).

Ching et al., "Tissue electrical properties monitoring for the prevention of pressure sore," *Prosthetics and Orthotics International*, 35(4):386-394 (2011).

Clendenin et al., "Inter-operator and inter-device agreement and reliability of the SEM Scanner," *Journal of Tissue Viability*, 24(1):17-23 (2015).

(56) References Cited

OTHER PUBLICATIONS

De Lorenzo et al., "Predicting body cell mass with bioimpedance by using theoretical methods: a technological review," *Journal of Applied Physiology*, 82(5):1542-1558 (1997).
Demarre et al., "The cost of pressure ulcer prevention and treatment in hospitals and nursing homes in Flanders: A cost-of-illness study," *International Journal of Nursing Studies*, 1-14 (2015).
Dodde et al., "Bioimpedance of soft tissue under compression," *Physiology Measurement*, 33(6):1095-1109 (2012).
DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).
Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).
DuPont, "Pyralux® FR Copper-clad Laminate," webpage, Retrieved from: www2.dupont.com/Pyraluxlen_US/ productsllaminate/FR/pyralux_fr.html, pp. 1-2 (2012).
Eberlein-Gonska et al., "The Incidence and Determinants of Decubitus Ulcers in Hospital Care: An Analysis of Routine Quality Management Data at a University Hospital," *Deutsches Arzteblatt International*, 110(33-34):550-556 (2013).
European Patent Office, ESSR issued on Aug. 22, 2014 for corresponding European Patent Application No. 11781106l.4 (pp. 1-7) and pending claims (pp. 3-10) pp. 1-10.
European Patent Office, Office Action dated Jul. 13, 2015, for corresponding European Patent Application No. 11781061.4 (pp. 1-5) and claims (pp. 6-9) pp. 1-9.
Extended European Search Report dated Aug. 19, 2016, in European Patent Application No. 16169670.
Extended European Search Report dated Sep. 19, 2016, in European Patent Application No. 16166483.4.
Extended European Search Report dated Mar. 13, 2017, in European Patent Application No. 16196899.5.
Gabriel, "Compilation of the Dielectric Properties of Body Tissues at Rf and Microwave Frequencies Report," *Occupational and Environmental Health Directorate*, (1996).
Gabriel et al., "The dielectric properties of biological tissues: II. Measurements in the frequency range 10 Hz to 20 GHz," *Physics in Medicine and Biology*, 41:2251-69 (1996).
Gardiner et al., "Incidence of hospital-acquired pressure ulcers—a population-based cohort study," *International Wound Journal*, 11(6):696-700 (2014).
Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).
Gonzalez-Correa et al., "Electrical bioimpedance readings increase with higher pressure applied to the measuring probe," *Physiology Measurement*, 26:S39-S47 (2005).
Guihan et al., "Assessing the feasibility of subepidermal moisture to predict erythema and stage 1 pressure ulcers in persons with spinal cord injury: A pilot study," *Journal of Spinal Cord Medicine*, 35(1):46-52 (2012).
Harrow, "Subepidermal moisture surrounding pressure ulcers in persons with a spinal cord injury: A pilot study," *Journal of Spinal Cord Medicine*, 37(6):719-728 (2014).
Houwing et al., "Pressure-induced skin lesions in pigs: reperfusion injury and the effects of vitamin E," *Journal of Wound Care*, 9(1):36-40 (2000).
Huang et al., "A device for skin moisture and environment humidity detection," *Sensors and Actuators B: Chemical*, 206-212 (2008).
International Search Report dated Apr. 12, 2018, issued in International Patent Application No. PCT/US2018/016731.
International Search Report dated Apr. 12, 2018, issued in International Patent Application No. PCT/US2018/016738.
International Search Report dated Apr. 26, 2018, issued in International Patent Application No. PCT/US2018/016741.
International Search Report dated Jul. 12, 2018, issued in International Patent Application No. PCT/US2018/016736.
International Search Report and Written Opinion dated Feb. 9, 2012 for International Patent Application No. PCT/US2011/035618.
International Search Report and Written Opinion dated Jul. 22, 2016, for International Patent Application No. PCT/US2016/28515.
International Search Report and Written Opinion dated Jul. 26, 2016, for International Patent Application No. PCT/US2016/28516.
International Search Report dated Sep. 10, 2018, issued in International Patent Application No. PCT/US2018/038055.
International Search Report dated Jan. 29, 2019, issued in International Patent Application No. PCT/US2018/061494.
International Search Report dated Feb. 5, 2019, issued in International Patent Application No. PCT/US2018/064527.
International Search Report dated Feb. 11, 2019, issued in International Patent Application No. PCT/US2018/061497.
Jan et al., "Local cooling reduces skin ischemia under surface pressure in rats: an assessment by wavelet analysis of laser Doppler blood flow oscillations," *Physiology Measurement*, 33(10):1733-1745 (2012).
Jaskowski, "Evaluation of the Healing Process of Skin Wounds by Means of Skin Absolute Value of Electrical Impedance," *Dermatol. Mon.schr.*, 172(4):223-228 (1986).
Jiang et al., "Expression of cytokines, growth factors and apoptosis-related signal molecules in chronic pressure ulcer wounds healing," *Spinal Cord*, 52(2):145-151 (2014).
Jiang et al., "Ischemia-Reperfusion Injury-Induced Histological Changes Affecting Early Stage Pressure Ulcer Development in a Rat model," *Ostomy Wound Management*, 57:55-60 (2011).
Jiricka et al., "Pressure Ulcer Risk factors in an ICU Population," *American Journal of Critical Care*, 4:361-367 (1995).
Kanai et al., "Electrical measurement of fluid distribution in legs and arms," *Medical Progress through Technology Journal*, 12:159-170 (1987).
Kasyua et al., "Potential application of in vivo imaging of impaired lymphatic duct to evaluate the severity of pressure ulcer in mouse model," *Scientific Reports*, 424173 (2014).
Lee, "CapSense Best Practices," *Application Note 2394*, 1-10 (2007).
Loerakker et al., "The effects of deformation, ischemia, and reperfusion on the development of muscle damage during prolonged loading," *Journal of Applied Physiology*, 111(4):1168-1177 (2011).
Loerakker et al., "Temporal Effects of Mechanical Loading on Deformation-Induced Damage in Skeletal Muscle Tissue," *Annual Review of Biomedical Engineering*, 38(8):2577-2587 (2010).
Lyder et al., "Quality of Care for Hospitalized Medicare Patients at Risk for Pressure Ulcers," *Archives of Internal Medicine*, 161:1549-1554 (2001).
Martinsen, "Bioimpedance and Bioelectricity Basics," *Elsevier Academic Press*, Chapters 1 and 10 (2015).
Mathiesen et al., "Are labour-intensive efforts to prevent pressure ulcers cost-effective?" *Journal of Medical Economics*, 16(10):1238-1245 (2013).
Matthie et al., "Analytic assessment of the various bioimpedance methods used to estimate body water," *Journal of Applied Physiology*, 84(5):1801-1816 (1998).
Miller et al., "Lymphatic Clearance during Compressive Loading," *Lymphology*, 14(4):161-166 (1981).
Moore et al., "A randomised controlled clinical trial of repositioning, using the 30° tilt, for the prevention of pressure ulcers," *Journal of Clinical Nursing*, 20:2633-2644 (2011).
Moore et al., "Pressure ulcer prevalence and prevention practices in care of the older person in the Republic of Ireland," *Journal of Clinical Nursing*, 21:362-371 (2012).
Moore et al., "A review of PU prevalence and incidence across Scandinavia, Iceland and Ireland (Part 1)", *Journal of Wound Care*, 22(7):361-362, 364-368 (2013).
Mulasi, "Bioimpedance at the Bedside: Current Applications, Limitations, and Opportunities," *Nutritional Clinical Practice*, 30(2):180-193 (2015).
National Pressure Ulcer Advisory Panel et al., "Prevention and Treatment of Pressure Ulcers: Clinical Practice Guideline," *Cambridge Media*, (2014).

(56) References Cited

OTHER PUBLICATIONS

Nixon et al., "Pathology, diagnosis, and classification of pressure ulcers: comparing clinical and imaging techniques," *Wound Repair and Regeneration*, 13(4):365-372 (2005).
Nuutinen et al., "Validation of a new dielectric device to asses changes of tissue water in skin and subcutaneous fat," *Physiological Measurement*, 25:447-454 (2004).
O'Goshi, "Skin conductance; validation of Skicon-200EX compared to the original model, Skicon-100," *Skin Research and Technology*, 13:13-18 (2007).
Oomens et al., "Pressure Induced Deep Tissue Injury Explained," *Annual Review of Biomedical Engineering*, 43(2):297-305 (2015).
Scallan et al., "Chapter 4: Pathophysiology of Edema Formation," *Capillary Fluid Exchange: Regulation, Functions, and Pathology*, 47-61 (2010).
Schultz et al., "Extracellular matrix: review of its role in acute and chronic wounds," *World Wide Wounds*, 1-20 (2005).
Schwan, "Electrical properties of tissues and cells," *Advances in Biology and Medical Physics*, 15:148-199 (1957).
Sener et al., "Pressure ulcer-induced oxidative organ injury is ameliorated by beta-glucan treatment in rats," *International Immunopharmacology*, 6(5):724-732 (2006).
Sewchuck el al., "Prevention and Early Detection of Pressure Ulcers in Patients Undergoing Cardiac Surgery," *AORN Journal*, 84(1):75-96 (2006).
Sprigle et al., "Analysis of Localized Erythema Using Clinical Indicators and Spectroscopy," *Ostomy Wound Management*, 49:42-52 (2003).
Stekelenburg et al., "Deep Tissue Injury: How Deep is Our Understanding?" *Archives of Physical Medicine Rehabilitation*, 89(7):1410-1413 (2008).
Stekelenburg et al., "Role of ischemia and deformation in the onset of compression-induced deep tissue injury: MRI-based studies in a rat model," *Journal of Applied Physiology*, 102:2002-2011 (2007).
Swisher et al., "Impedance sensing device enables early detection of pressure ulcers in vivo," *Nature Communications*, 6:6575-6584 (2015).
Thomas et al., "Hospital-Acquired Pressure Ulcers and Risk of Death," *Journal of the American Geriatrics Society*, 44:1435-1440 (1996).
Valentinuzzi et al., "Bioelectrical Impedance Techniques in Medicine. Part II: Monitoring of Physiological Events by Impedance," *Critical Reviews in Biomedical Engineering*, 24(4-6):353-466 (1996).
Vangilder et al., "Results of Nine International Pressure Ulcer Prevalence Surveys: 1989 to 2005," *Ostomy Wound Management*, 54(2):40-54 (2008).
Wagner et al., "Bioelectrical Impedance as a Discriminator of Pressure Ulcer Risk," *Advances in Wound Care*, 9(2):30-37 (1996).
Wang, "Biomedical System for Monitoring Pressure Ulcer Development," UCLA Electronic Theses and Dissertations, California, USA, pp. 1-123 (2013).
Watanabe et al., "CT analysis of the use of the electrical impedance technique to estimate local oedema in the extremities in patients with lymphatic obstruction," *Medical and Biological Engineering and Computing*, 36(1):60-65 (1998).
Weiss, "Tissue destruction by neutrophils," *The New England Journal of Medicine*, 320(6):365-76 (1989).
International Search Report dated May 29, 2019, issued in International Patent Application No. PCT/US2019/017226.
Bates-Jensen et al., "Subepidermal Moisture Detection of Pressure Induced Tissue Damage on the Trunk: The Pressure Ulcer Detection Study Outcomes," Wound Repair and Regeneration, 25:502-511 (2017).
Berggren, "Capacitive Biosensors," Electroanalysis, 13(3):173-180 (2001), Wiley-VCH (publisher), Weinheim, Germany.
Black et al., "Differential Diagnosis of Suspected Deep Tissue Injury," International Wound Journal, 13(4):531-539 (2015)
Brem et al., "Protocol for the Successful Treatment of Pressure Ulcers," The American Journal of Surgery, 188 (Suppl. to Jul. 2004):9S-17S (2004).
De Oliveira et al., "Sub-epidermal moisture versus tradition and visual skin assessments to assess pressure ulcer risk in surgery patients," Journal of Wound Care, 31(3):254-264 (2022), Mark Allen Group (pub.) (obtained online).
Extended European Search Report dated Oct. 25, 2019, in European Patent Application No. 19186393.5.
Extended European Search Report dated Nov. 19, 2019, in European Patent Application No. 19190000.0.
Extended European Search Report dated Feb. 6, 2020, in European Patent Application No. 18748733.5.
Extended European Search Report dated Feb. 10, 2020, in European Patent Application No. 18748025.6.
Extended European Search Report dated Feb. 10, 2020, in European Patent Application No. 18748512.3.
Extended European Search Report dated Jun. 24, 2020, in European Patent Application No. 18747707.0.
Extended European Search Report dated Mar. 17, 2022, in European Patent Application No. 19838240.0.
Extended European Search Report dated May 24, 2022, in European Patent Application No. 19871332.3.
Extended European Search Report dated Feb. 1, 2023, in European Patent Application No. 22211200.
Ford, "Hospice Wins Award for Innovation in Pressure Ulcer Prevention," Nursing Times, downloaded and printed on Apr. 18, 2020, from https://www.nursingtimes.net/news/research-and-innovation/hospice-wins-award-for-innovation-in-pressure-ulcer-prevention-30-11-2018/ (2018).
Great Britain Search Report dated Apr. 27, 2020, in Great Britain Patent Application No. GB2002889.0.
Great Britain Search Report dated Jun. 28, 2021, in Great Britain Patent Application No. GB2106848.1.
Great Britain Search Report dated Feb. 9, 2022, in Great Britain Patent Application No. GB2118088.0.
Great Britain Search Report dated Feb. 14, 2022, in Great Britain Patent Application No. GB2118092.2.
Hamazoto et al., "Estimate of Burn Depth by Non-Invasive Capacitance Measurement," Japan Soc. ME & BE, 42:266 (Jun. 2003).
Hou, "Section IV. Osteofascial Compartment Syndrome," Limbs Trauma, 7:215-217 (2016), Hubei Science & Technology Publishing House (pub.), Wuhan, China.
International Search Report dated Mar. 9, 2020, issued in International Patent Application No. PCT/US2019/055655.
International Search Report dated Dec. 8, 2020, issued in International Patent Application PCT/US2020/051134.
International Search Report dated Aug. 17, 2021, issued in International Patent Application PCT/US2021/023818.
International Search Report dated May 13, 2022, issued in International Patent Application PCT/US2022/014913.
International Search Report dated Aug. 2, 2022, issued in International Patent Application PCT/US2022/025508.
International Search Report dated Aug. 15, 2022, issued in International Patent Application PCT/US2022/019338.
Liu et al., "A Systematic Review of Electrical Stimulation for Pressure Ulcer Prevention and Treatment in People with Spinal Cord Injuries," The Journal of Spinal Cord Medicine, 37(6):703-718 (2014).
Moore et al., "Subepidermal Moisture (SEM) and Bioimpedance: A Literature Review of a Novel Method for Early Detection of Pressure-Induced Tissue Damage (Pressure Ulcers)," International Wound Journal, 14(2):331-337 (2016).
Moore, "Using SEM (Sub Epidermal Moisture) Measurement for Early Pressure Ulcer Detection," Institute for Pressure Injury Prevention, WCICT 2017 (Jun. 20-21), Manchester, UK, 7 pp., available at www.pressureinjuryprevention.com/wp-content/uploads/2017/07/ipip_Moore_Sub_Epidermal_Moisture_notes.pdf (2017) (obtained online).
Moore et al., "SEM Scanner Made Easy," Wounds International, pp. 1-6, available at www.woundsinternational.com (2018).
Musa et al., "Clinical impact of a sub-epidermal moisture scanner: what is the real-world use?," J. Wound Care, 30(3):2-11 (2021), Mark Allen Group (pub.) (obtained online).

(56) References Cited

OTHER PUBLICATIONS

Oliveira, "The Accuracy of Ultrasound, Thermography, Photography and Sub-Epidermal Moisture as a Predictor of Pressure Ulcer Presence—a Systematic Review," RCSI, School of Nursing thesis (2015).

Pang et al. (eds.) *Diagnosis and Treatment of Diabetes*, China Press of Traditional Chinese Medicine (publisher), Beijing, China, pp. 466-468 (Oct. 2016), with English Translation.

Rotaru et al., "Friction between Human Skin and Medical Textiles for Decubitus Prevention," *Tribology International*, 65:91-96 (2013).

Saxena, *The Pocket Doctor: Obstetrics & Gynecology*, pp. 76-77 (2017), Tianjin Science & Technology Translation & Publishing Co. Ltd. (pub.), Tianjin, China.

Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49 pp. (Aug. 2019).

Supplementary Partial European Search Report dated Jan. 27, 2020, in European Patent Application No. 18747707.

Supplementary European Search Report dated Jul. 13, 2021, in European Patent Application No. 18887039.

Supplementary European Search Report dated Oct. 1, 2021, in European Patent Application No. 19751130.

Thomas, "Prevention and Treatment of Pressure Ulcers," *J. Am. Med. Dir. Assoc.*, 7:46-59 (2006).

Truong et al., "Pressure Ulcer Prevention in the Hospital Setting Using Silicone Foam Dressings," *Cureus*, 8(8):e730, pp. 1-6 (2016).

Tur et al., "Topical Hydrogen Peroxide Treatment of Ischemic Ulcers in the Guinea Pig: Blood Recruitment in Multiple Skin Sites," *J. Am. Acad. Dermatol.*, 33:217-221 (1995).

Vowden et al., "Diabetic Foot Ulcer or Pressure Ulcer? That Is the Question," *The Diabetic Foot Journal*, 18:62-66 (2015).

Wang et al., "A Wireless Biomedical Instrument for Evidence-Based Tissue Wound Characterization," *Wireless Health*, pp. 222-223 (2010).

Yang, *Handbook of Practical Burn Surgery*, p. 48 (2008), People's Military Medical Press (pub.), Beijing, China.

Zanibbi, "Pattern Recognition: An Overview," downloaded from https://www.cs.rit.edu/~rlaz/prec20092/slides/Overview.pdf, 30 pp. (2010).

\* cited by examiner

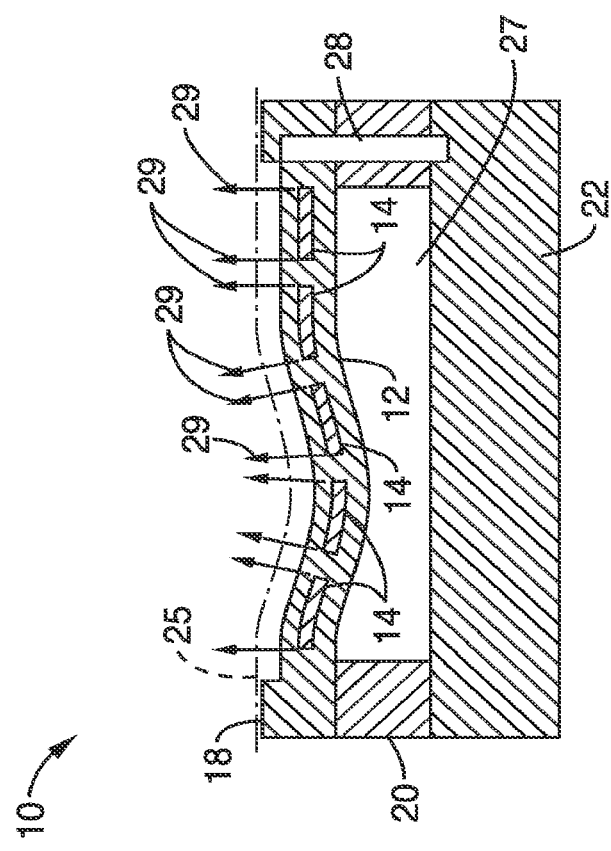
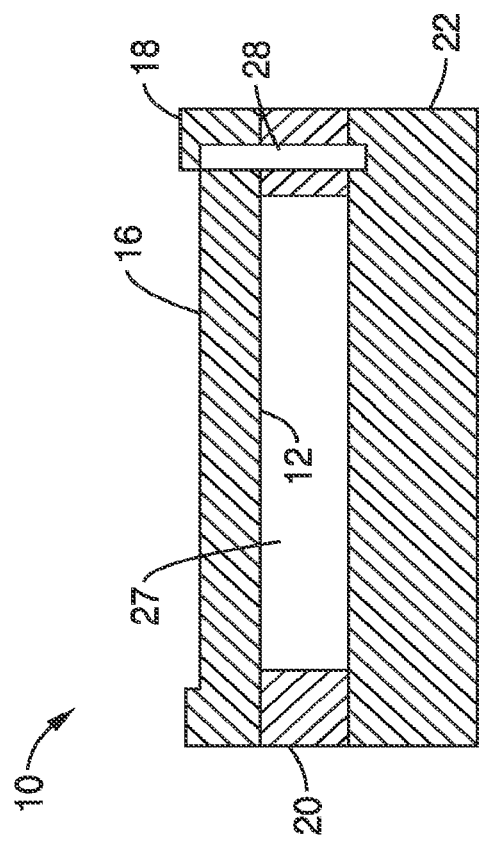

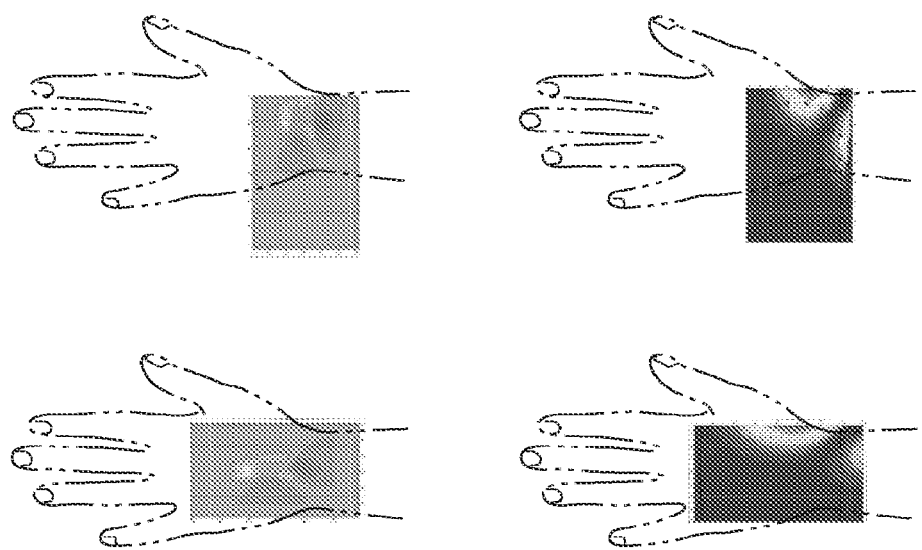

SEM SCANNER SENSING APPARATUS, SYSTEM AND METHODOLOGY FOR EARLY DETECTION OF ULCERS

CROSS-REFERENCE TO RELATED APPLICATIONS

This application is a continuation of U.S. patent application Ser. No. 16/210,911 filed on Dec. 5, 2018, incorporated herein by reference in its entirety, which is a continuation of U.S. patent application Ser. No. 15/095,046 filed on Apr. 9, 2016, now U.S. Pat. No. 10,188,340, issued on Jan. 29, 2019, incorporated herein by reference in its entirety, which is a continuation of U.S. patent application Ser. No. 15/058,964 filed on Mar. 2, 2016, now U.S. Pat. No. 9,980,673, issued on May 29, 2018, incorporated herein by reference in its entirety, which is a continuation of U.S. patent application Ser. No. 14/827,375 filed on Aug. 17, 2015, now U.S. Pat. No. 9,398,879, issued on Jul. 26, 2016, incorporated herein by reference in its entirety, which is a continuation of U.S. patent application Ser. No. 14/297,977 filed on Jun. 6, 2014, now U.S. Pat. No. 9,220,455, issued on Dec. 29, 2015, incorporated herein by reference in its entirety, which is a continuation of U.S. patent application Ser. No. 13/668,047 filed on Nov. 2, 2012, incorporated herein by reference in its entirety, which is a 35 U.S.C. § 111(a) continuation of PCT international application number PCT/US2011/035618 filed on May 6, 2011, incorporated herein by reference in its entirety, which claims the benefit of U.S. provisional patent application Ser. No. 61/332,755 filed on May 8, 2010, incorporated herein by reference in its entirety, and which claims the benefit of U.S. provisional patent application Ser. No. 61/453,852 filed on Mar. 17, 2011, incorporated herein by reference in its entirety. Priority is claimed to each of the foregoing applications.

The above-referenced PCT international application was published as PCT International Publication No. WO 2011/143071 on Nov. 17, 2011 and republished on Apr. 5, 2012, and is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to monitoring skin pressure ulcers and more particularly to skin ulcer monitoring via measurement of Sub-epidermal Moisture (SEM).

2. Description of Related Art

Patients' skin integrity has long been an issue of concern for nurses and in nursing homes. Maintenance of skin integrity has been identified by the American Nurses Association as an important indicator of quality nursing care. Meanwhile, pressure ulcers remain a major health problem particularly for hospitalized older adults. When age is considered along with other risk factors, the incidence of pressure ulcers is significantly increased. Overall incidence of pressure ulcers for hospitalized patients ranges from 2.7% to 29.5%, and rates of greater than 50% have been reported for patients in intensive care settings. In a multicenter cohort retrospective study of 1,803 older adults discharged from acute care hospitals with selected diagnoses, 13.2% (i.e., 164 patients) demonstrated an incidence of stage I ulcers. Of those 164 patients, 38 (16%) had ulcers that progressed to a more advanced stage. Pressure ulcers additionally have been associated with an increased risk of death one year after hospital discharge. The estimated cost of treating pressure ulcers ranges from $5,000 to $40,000 for each ulcer, depending on severity.

Therefore, there is an urgent need to develop a preventive solution to measure moisture content of the skin as a mean to detect early symptoms of ulcer development.

BRIEF SUMMARY OF THE INVENTION

An aspect of the present invention is a smart compact capacitive sensing conforming handheld apparatus configured to measure Sub-epidermal Moisture (SEM) as a mean to detect and monitor the development of pressure ulcers. The device incorporates an array of electrodes which are excited to measure and scan SEM in a programmable and multiplexed manner by a battery-less RF-powered chip. The scanning operation is initiated by an interrogator which excites a coil embedded in the apparatus and provides the needed energy burst to support the scanning/reading operation. Each embedded electrode measures the equivalent sub-epidermal capacitance corresponding and representing the moisture content of the target surface.

An aspect of this invention is the in situ sensing and monitoring of skin or wound or ulcer development status using a wireless, biocompatible RF powered capacitive sensing system referred to as smart SEM imager. The present invention enables the realization of smart preventive measures by enabling early detection of ulcer formation or inflammatory pressure which would otherwise have not been detected for an extended period with increased risk of infection and higher stage ulcer development.

In one beneficial embodiment, the handheld capacitive sensing imager apparatus incorporates pressure sensing components in conjunction with the sensing electrodes to monitor the level of applied pressure on each electrode in order to guarantee precise wound or skin electrical capacitance measurements to characterize moisture content. In summary, such embodiment would enable new capabilities including but not limited to: 1) measurement capabilities such as SEM imaging and SEM depth imaging determined by electrode geometry and dielectrics, and 2) signal processing and pattern recognition having automatic and assured registration exploiting pressure imaging and automatic assurance of usage exploiting software systems providing usage tracking.

One major implication of this sensor-enhanced paradigm is the ability to better manage each individual patient resulting in a timelier and more efficient practice in hospitals and even nursing homes. This is applicable to patients with a history of chronic wounds, diabetic foot ulcers, pressure ulcers or post-operative wounds. In addition, alterations in signal content may be integrated with the activity level of the patient, the position of patient's body and standardized assessments of symptoms. By maintaining the data collected in these patients in a signal database, pattern classification, search, and pattern matching algorithms can be developed to better map symptoms with alterations in skin characteristics and ulcer development. This approach is not limited to the specific condition of ulcer or wound, but may have broad application in all forms of wound management and even skin diseases or treatments.

One aspect is apparatus for sensing sub-epidermal moisture (SEM) from a location external to a patient's skin. The apparatus includes a bipolar RF sensor embedded on a flexible substrate, and a conformal pressure pad disposed adjacent and underneath the substrate, wherein the conformal pressure pad is configured to support the flexible substrate while allowing the flexible substrate to conform to a non-planar sensing surface of the patient's skin. The apparatus further includes interface electronics coupled to the sensor; wherein the interface electronics are configured to control emission and reception of RF energy to interrogate the patient's skin.

Another aspect is a method for monitoring the formation of pressure ulcers at a target location of a patient's skin. The method includes the steps of positioning a flexible substrate adjacent the target location of the patient's skin; the flexible substrate comprising one or more bipolar RF sensors; conforming the flexible substrate to the patient's skin at the target location; exciting the one or more bipolar RF sensor to emit RF energy into the patient's skin; and measuring the capacitance of the skin at the target location as an indicator of the Sub-Epidermal Moisture (SEM) at the target location.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 8 illustrates a schematic side view of the SEM scanner of FIG. 1.

FIG. 9 illustrates a schematic side view of the SEM scanner of FIG. 8 in contact with subject skin.

FIG. 20 illustrates sample measurements over two different days.

DETAILED DESCRIPTION OF THE INVENTION

In one exemplary embodiment, a smart handheld capacitive sensing device according to the present invention employs a programmable sensing electrode array. This is based on methods that use an interrogator to excite the embedded electrodes.

Figure 1:
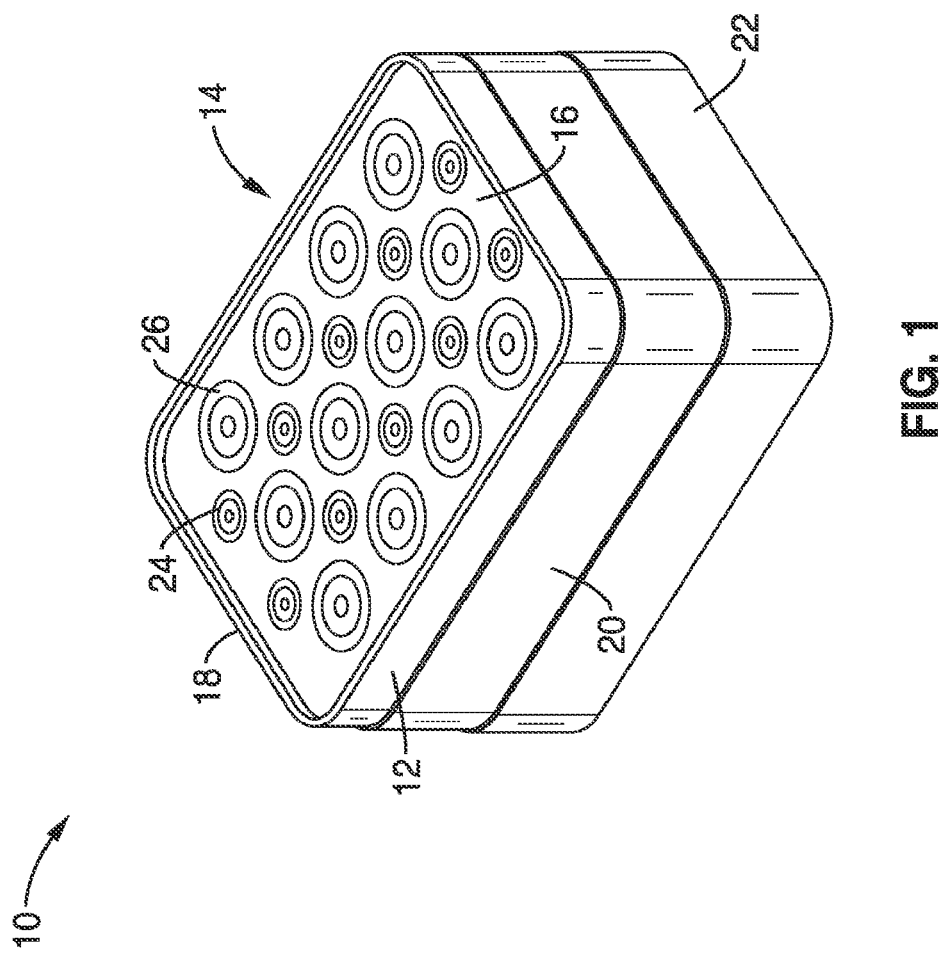
FIG. 1 illustrates an assembled perspective component view of the SEM Scanner of the present invention.
Figure 7:
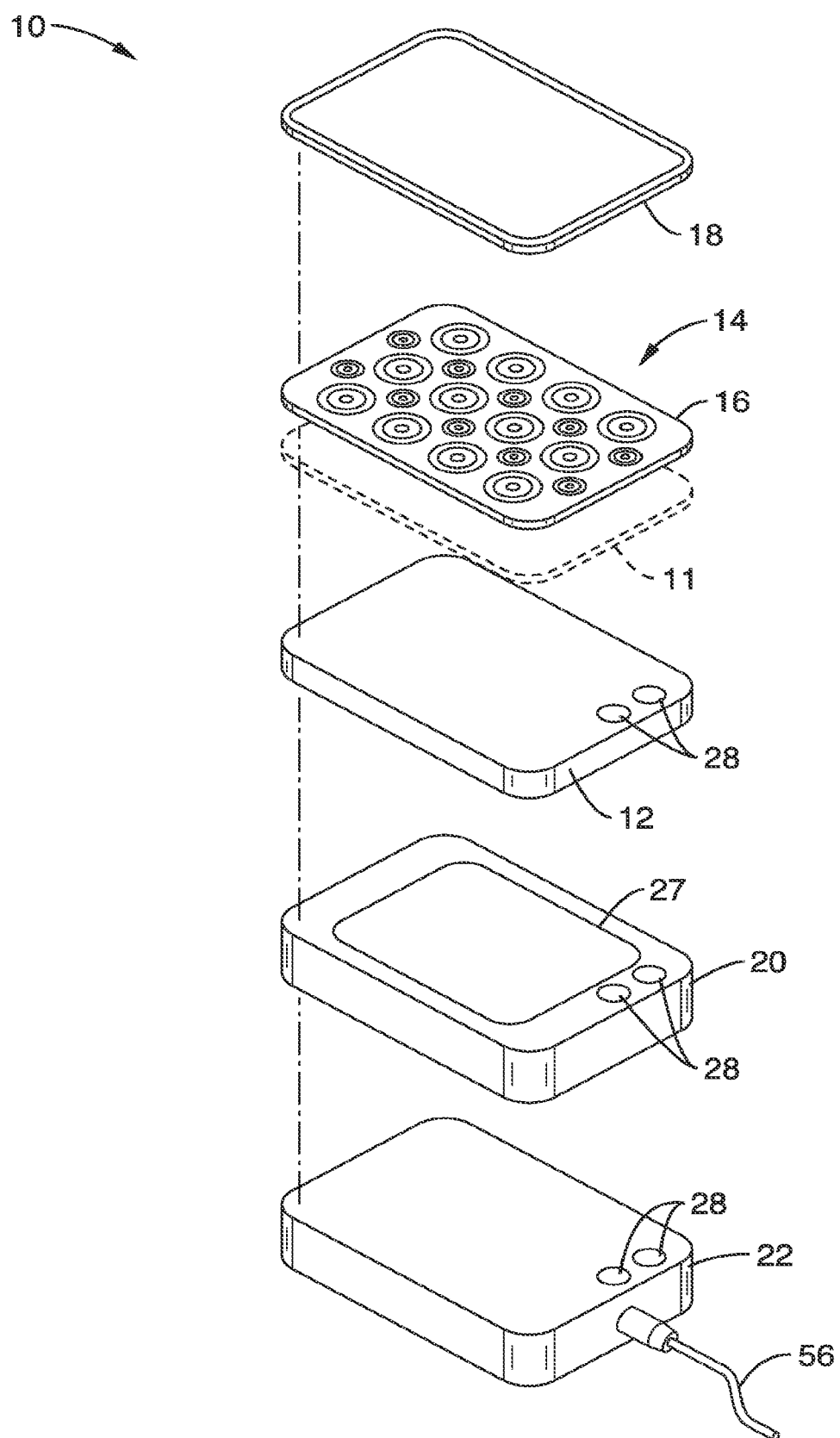
FIG. 7 illustrates an exploded perspective component view of the SEM scanner of FIG. 1.

FIG. 1 and FIG. 7 illustrate an SEM scanning/sensing apparatus 10 according to the present invention. The apparatus 10 comprises five main components, including a top silicone edge sealing gasket 18 encircling a Kapton-based sensing substrate 16, which rests on a conformal silicone pressure pad 12. A thick annular silicone spacer 20 is disposed under the pressure pad to provide free space for the pressure pad to deform. The bottom layer comprises an interface electronics package enclosure 22 that houses interface circuitry for interrogating and transmitting data for evaluation. These five main components are described in further detail below.

In the embodiment shown in FIG. 1, an array 14 of individual RF electrode sensors 24 and 26 is embedded on a flexible biocompatible substrate 16. Substrate 16 may comprise a laminated Kapton (Polyimide) chip-on-flex.

Figure 2:
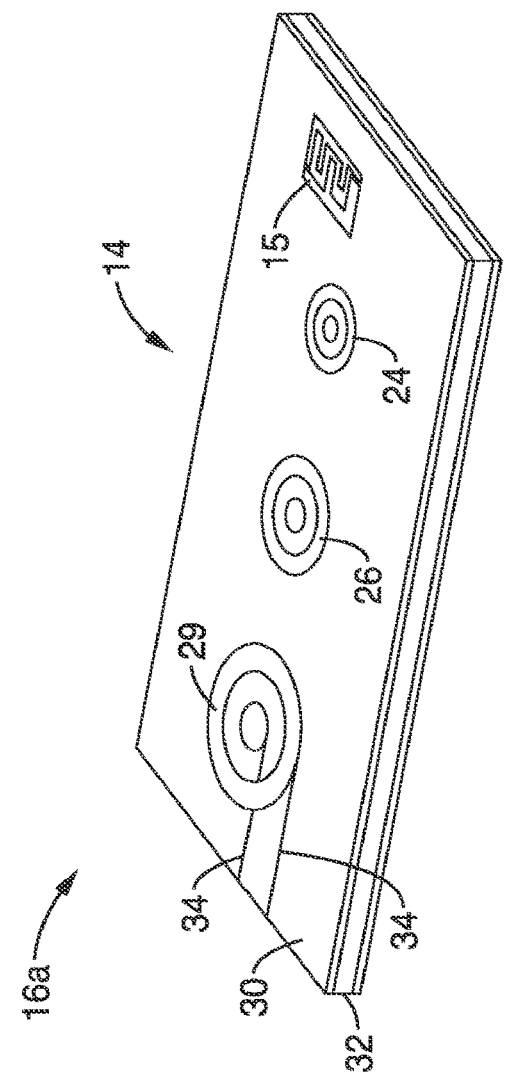
FIG. 2 illustrates a perspective view of a Kapton-based conforming sensing substrate assembly of the present invention.

FIG. 2 illustrates one embodiment of a Kapton sensor substrate 16a that comprises an array 14 of differing sized concentric sensing electrodes. A flexible biocompatible Polyimide or Kapton substrate 32 comprises a layer of sensing electrodes coated on one side with an ultra thin cover layer 30 of Polyimide (e.g. CA335) to isolate the electrodes from direct moisture contact and also to provide a uniform contact surface.

In FIG. 2, sample capacitive sensing electrodes of different sizes (e.g. 24, 26, and 29) are shown in an array 14, and which are manipulated to achieve and sense different depths of skin. The array of sensing electrodes 14 may comprise any number of different shape and configurations, such as the concentric circles 24, 26, 29, or the interdigitating fingers of sensor 15.

Figure 3:
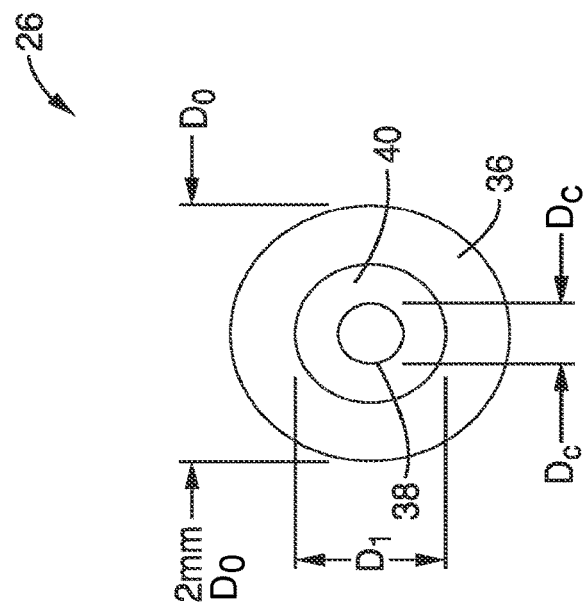
FIG. 3 shows a top view of an exemplary concentric sensing electrode in accordance with the present invention.

FIG. 3 illustrates a close-up top view of a concentric sensing pad 26 in accordance with the present invention. Pad 26 comprises a bipolar configuration having a first electrode 36 comprising an outer annular ring disposed around a second inner circular electrode 38. Outer ring electrode 36 has an outer diameter $D_o$ and an inner diameter $D_i$ that is larger than the diameter $D_c$ of the circular inner electrode 38 to form annular gap 40. Inner circular electrode 38 and outer ring electrode 36 are coupled electrically to interface electronics in the interface electronics package 22. As shown in greater detail in FIGS. 4 and 5, electrodes 36 and 38 are disposed on separate layers within the substrate assembly 16.

The dimensions of the sensor pads 24, 26 generally correspond to the depth of interrogation into the derma of the patient. Accordingly, a larger diameter pad (e.g. pad 26 or 29) will penetrate deeper into the skin than a smaller pad. The desired depth may vary depending on the region of the body being scanned, or the age, skin anatomy or other characteristic of the patient. Thus, SEM scanner 10 may comprise an array of different sized pads (e.g. small pads 24 and medium sized pads 26 shown in FIG. 1) each individually coupled to the interface electronics package 22.

Figure 4:
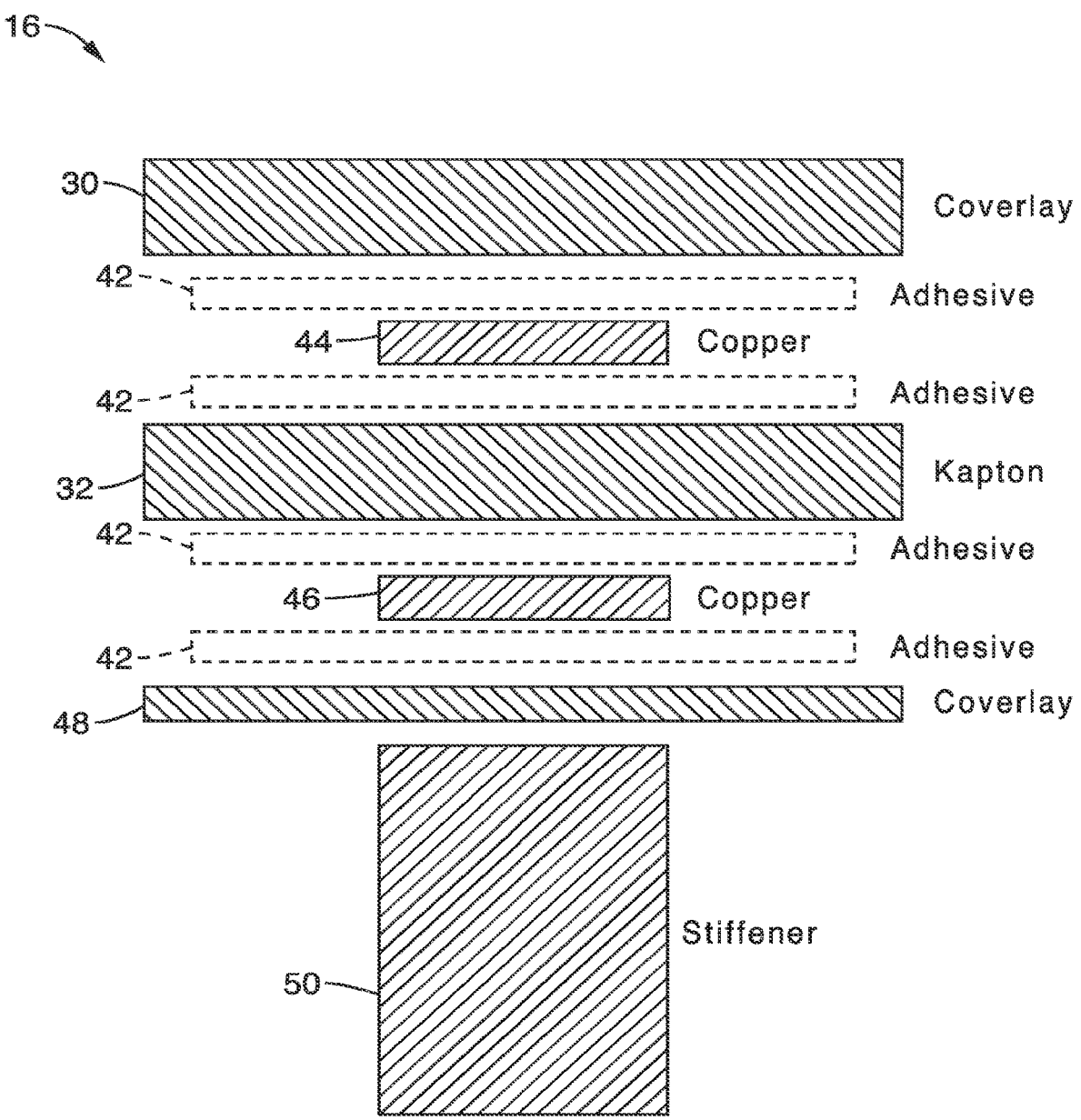
FIG. 4 illustrates a side view of a flex stack-up for the Kapton-based conforming sensing substrate shown in FIG. 2.

FIG. 4 illustrates side view of a flex stack-up for a Kapton based substrate assembly 16, where thin adhesive layers 42 are used to attach a Kapton layer 32 in between copper layers 44 and 46, all of which are disposed between upper coverlay 30 and lower coverlay 48. A stiffener 50 is disposed under lower coverlay 48, being positioned directly under copper layer 46 of the sensing pads. The stiffener 50 forms a rigid portion of the substrate where sensing pad array 14, connectors (e.g. connectors 66, 76, or 86 shown in FIG. 6) and interfacing (e.g. lead wires 34) are located, so that these areas do not deform, whereas the rest of the substrate is free to deform. The top copper layer 44 is used to etch out electrode array 14 and corresponding copper routing 34 to the connectors. The bottom copper layer 46 preferably comprises a crisscross ground plane to shield electrode array 14 from unwanted electromagnetic interference.

In one embodiment, the flex substrate 16 assembly comprises Pyralux FR material from Dupont. In an exemplary configuration, approximately 5 mil thick FR9150R double-sided Pyralux FR copper clad laminate is used as the Kapton substrate. Top coverlay 30 comprises Pyralux 5 mil FR0150 and the bottom coverlay 48 comprises 1 mil FR0110 Pyralux. The thickness of the top FR0150 coverlay 30 is an important parameter as it affects the sensitivity of sensing electrodes in measuring skin moisture content. Copper layers 44, 46 are generally 1.4 mil thick, while adhesive layers 42 are generally 1 mil thick. The stiffener 50 is shown in FIG. 4 is approximately 31 mil thick.

Figure 5:
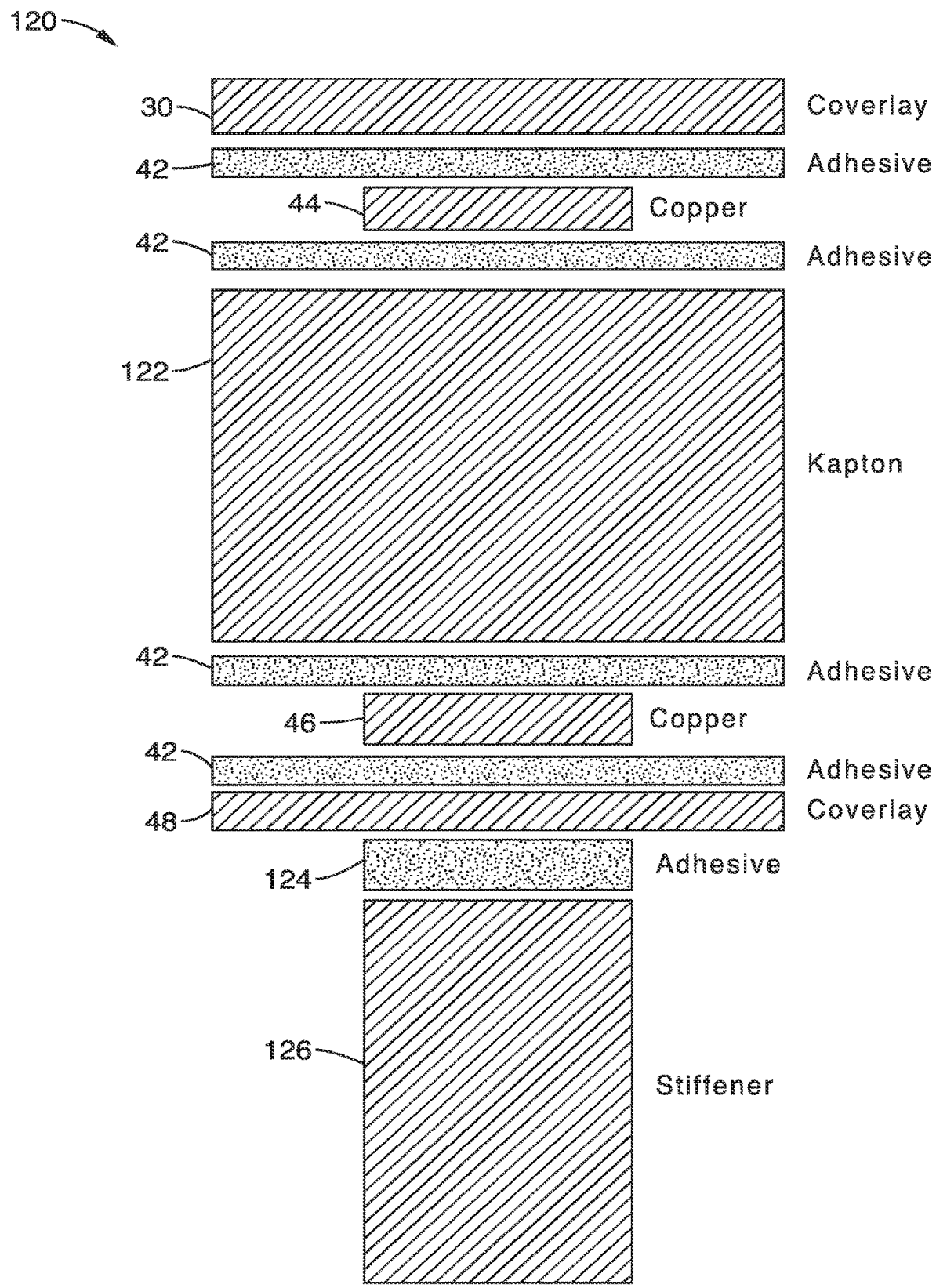
FIG. 5 illustrates a side view of an alternative flex stack-up for a Kapton-based conforming sensing substrate.

FIG. 5 shows a side view of a preferred alternative flex stack-up for a Kapton based substrate 120, where thin adhesive layers 42 (1 mil) are used to attach an 18 mil Kapton layer 122 in between 1.4 mil copper layers 44 and 46, all of which are disposed between 2 mil upper coverlay 30 and 1 mil lower coverlay 48. A stiffener 50 is disposed under lower coverlay 48, being positioned directly under copper layer 46 of the sensing pad. The 31 mil FR4 stiffener 126 forms a rigid portion of the substrate under the array 14 of sensing pads, connectors 66 and interfacing 34. A 2 mil layer of PSA adhesive 124 is used between the bottom coverlay 48 and stiffener 126. The layering of assembly 120 is configured to provide proper shielding from interference.

Figure 6:
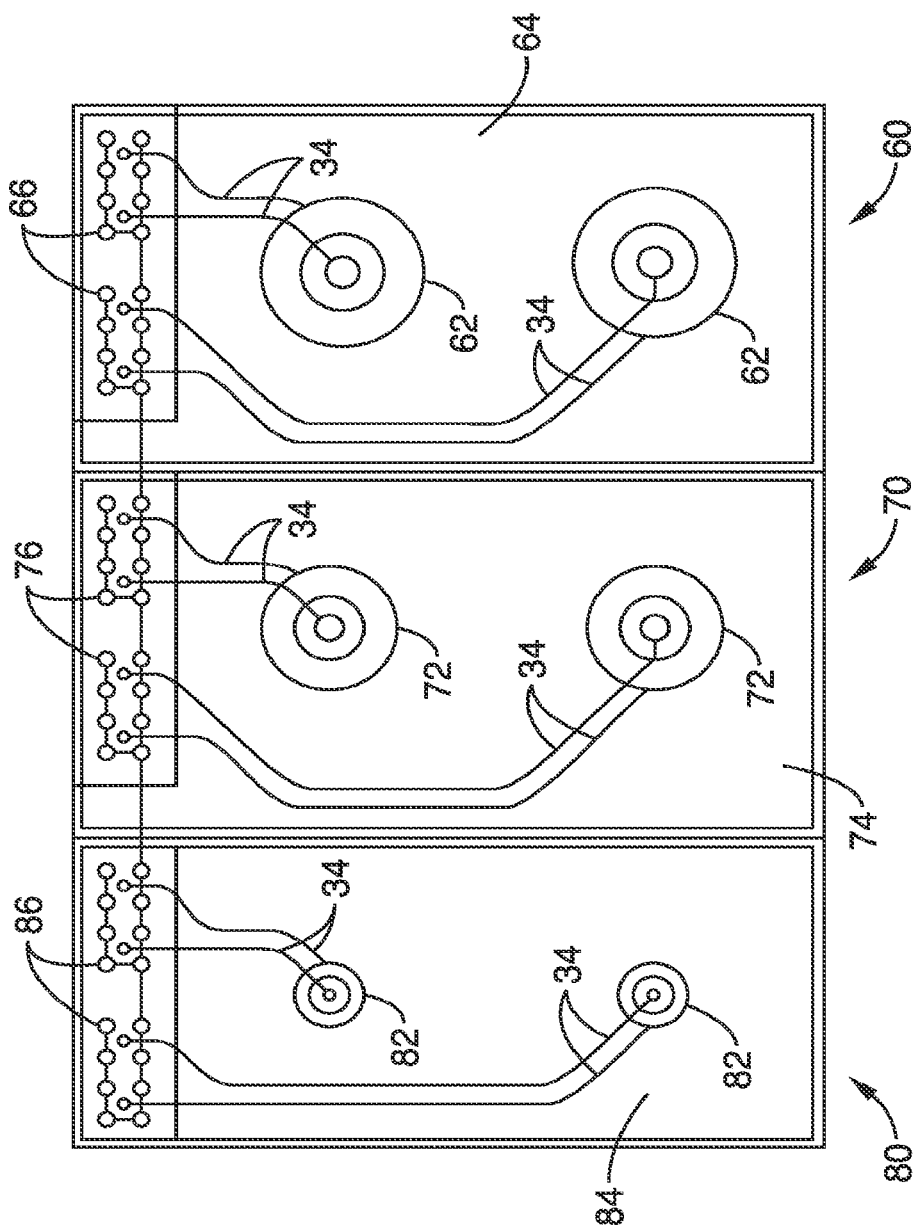
FIG. 6 shows a top view of two-electrode sensing Kapton-based flex sensor substrates for three alternative types of capacitive sensing concentric electrodes.

FIG. 6 shows a top view of three separate and adjacently arranged concentric bipolar electrode sensing Kapton-based flex pads 60, 70 and 80 having different sized capacitive sensing concentric electrodes. Pad 60 comprises a substrate having two large concentric electrodes 62 wired through substrate 64 via connectors 34 to lead line inputs 66. Pad 70 comprises a substrate having two medium concentric electrodes 72 wired through substrate 74 to lead line inputs 76. Pad 80 comprises a substrate having two small concentric electrodes 82 wired through substrate 84 to lead line inputs 86. The configuration shown in FIG. 6 is optimized for cutting/manufacturing and also to avoid interference between data lines and sensors. Each of the bipolar electrode pads is individually wired to the electronics package 22 to allow for independent interrogation, excitation, and data retrieval.

FIG. 7 illustrates an exploded perspective component view of the SEM scanner 10. The silicone edge sealing gasket 18 is applied over the Kapton sensor substrate assembly 16 to seal and shield the edge interface connectors through which interface electronics package 22 excite and controls the sensing electrode array 14. The Kapton sensor substrate assembly 16 rests on a conformal silicone pressure pad 12 that provides both support and conformity to enable measurements over body curvature and bony prominences.

In one beneficial embodiment, pressure sensor 11 may be embedded under each sensing electrode 24, 26 (e.g. in an identical array not shown), sandwiched between Kapton sensor substrate 26 and the conformal silicone pressure pad 28 to measure applied pressure at each electrode, thus ensuring a uniform pressure and precise capacitance sensing.

Lead access apertures 28 provide passage for routing the connector wires (not shown) from the substrate connectors (e.g. 66, 76, 86) through the pressure pad 12, annular spacer 20 to the interface electronics 22.

The annular silicone spacer 20 comprises a central opening 27 that provides needed spacing between the conformal silicone pressure pad 12 and the interface electronics package 22 to allow the pressure pad 12 and flexible substrate to conform in a non-planar fashion to conduct measurements over body curvatures or bony prominences.

In one embodiment, the interface electronics package 22 is connected to a logging unit or other electronics (not shown) through wire-line USB connector 56.

The interface electronics package 22 preferably comprises an enclosure that contains all the electronics (not shown) needed to excite, program and control the sensing operation and manage the logged data. The electronics package 22 may also comprise Bluetooth or other wireless communication capabilities to allow for transfer of sensing data to a computer or other remote device. Docked data transfer is also contemplated, in addition to real-time Bluetooth transfer. A gateway device (not shown) may be used for communicating with the SEM device 10 and data formatting prior to upload to a computer or backend server.

FIG. 8 is a schematic side view of the SEM scanner 10 in the nominal configuration, showing the edge gasket 18 over Kapton substrate 16, and lead access apertures 28, which provide access through annular spacer 20 and conformal pad 12 to electronics 22.

FIG. 9 illustrates a schematic side view of the SEM scanner 10 in contact with the target subject 25. The annular silicone spacer 20 provides enough spacing for conforming silicone pad 12 to conform to the target surface 25. The conforming silicone pad 12 enables continuous contact between the substrate 16 and patient's skin 25, thus minimizing gaps between the substrate 16 and patient's skin 25 that could otherwise result in improper readings of the patient anatomy. Electrode array 14, which is embedded in substrate 16, is shown interrogating into the derma of tissue 25 by directing emission of an RF signal or energy into the skin and receiving the signal and correspondingly reading the reflected signal. The interrogator or electronics package 22 excites electrode coil 14 by providing the needed energy burst to support the scanning/reading of the tissue. Each embedded electrode 14 measures the equivalent sub-epidermal capacitance corresponding to the moisture content of the target skin 25.

While other energy modalities are contemplated (e.g. ultrasound, microwave, etc.), RF is generally preferred for its resolution in SEM scanning.

Figure 10:
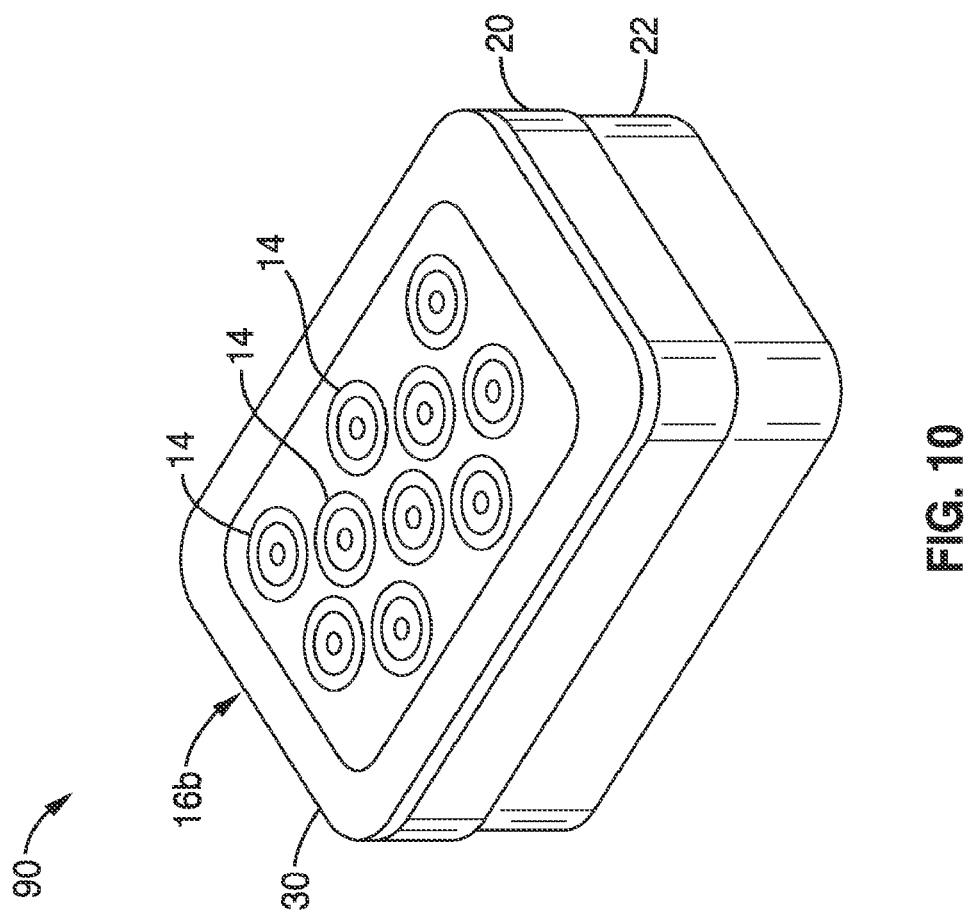
FIG. 10 illustrates a perspective view of an assembled SEM scanner with an alternative array of sensors in accordance with the present invention.

FIG. 10 illustrates a perspective view of an assembled SEM scanner 10 with an alternative substrate 16b having an array 14 of ten sensors dispersed within the substrate 16b. This larger array 14 provides for a larger scanning area of the subject anatomy, thus providing a complete picture of the target anatomy in one image without having to generate a scanning motion. It is appreciated that array 14 may comprise any number of individual sensors, in be disposed in a variety of patterns.

The SEM scanner 10 was evaluated using a number of different sized and types of sensors 26. Table 1 illustrates electrode geometries are used throughout the following measurements. As shown in FIG. 1 the outer ring electrode diameter $D_o$ varied from 5 mm for the XXS pad, to 55 mm for the large pad. The outer ring electrode inner diameter $D_i$ varied from 4 mm for the XXS pad, to 40 mm for the large pad. The inner electrode diameter $D_c$ varied from 2 mm for the XXS pad, to 7 mm for the large pad. It is appreciated that the actual dimensions of the electrodes may vary from ranges shown in these experiments. For example, the contact diameter may range from 5 mm to 30 mm, and preferably ranges from 10 mm to 20 mm.

To measure the properties of each sensor size listed in Table 1, the sensors were fabricated using both Kapton and rigid board. In testing with the rigid sensor pads, lotion was applied to the thumb continuously for 15 minutes.

Figure 11:
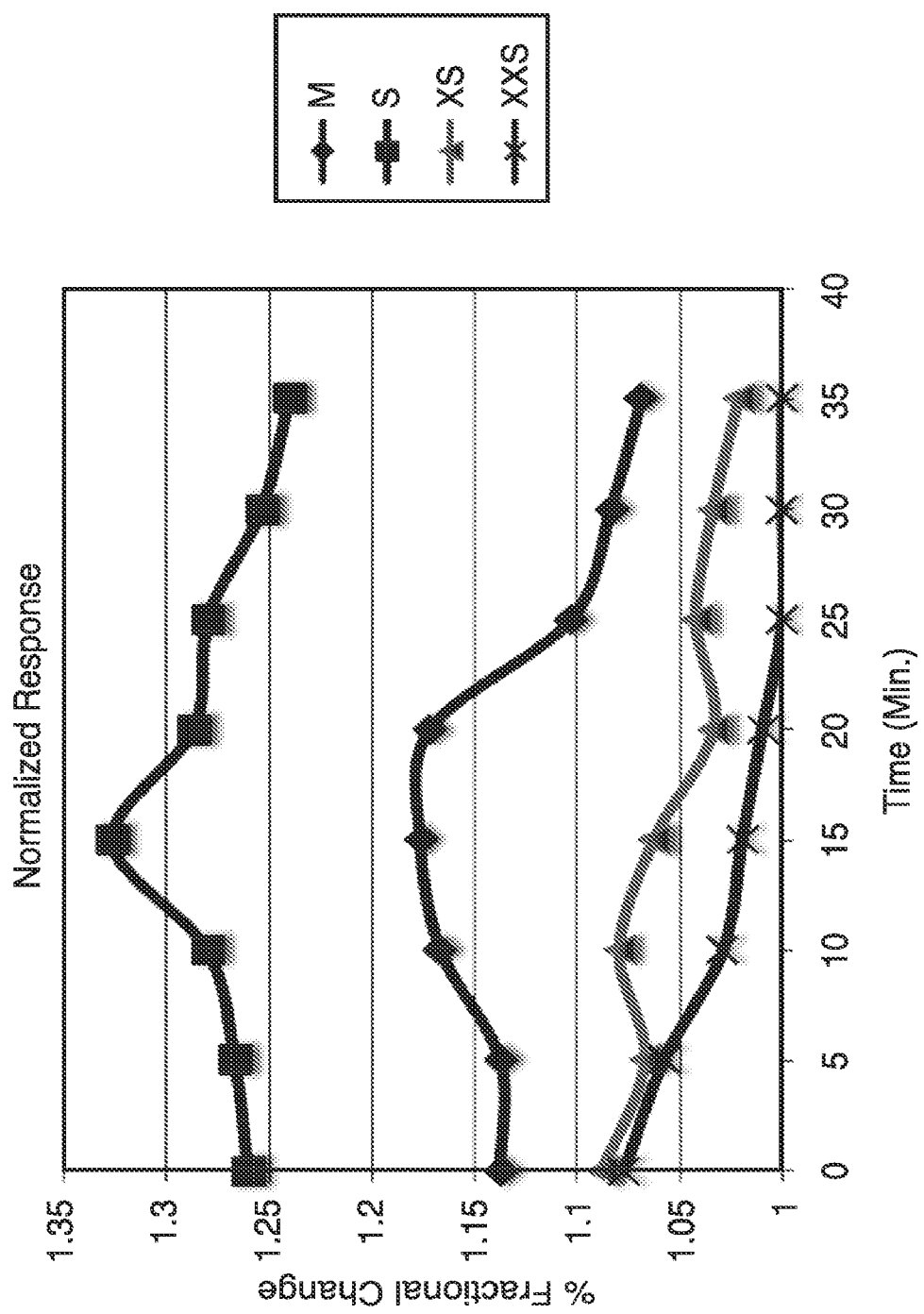
FIG. 11 is a plot of normalized responses of the tested electrodes of the present invention.

FIG. 11 is a plot of normalized responses of the tested electrodes of the present invention. The four sensors' (XXS, XS, S, M) normalized responses are compared in FIG. 11 and Table 2.

As can be seen in FIG. 11 and Table 2, the S electrode appears to be most responsive overall to the presence of moisture. Both the M and S electrodes seem to exhibit a peak. This suggests a depth dependency of the moisture being absorbed into the skin, as the roll-off from the M electrode occurs about 5 minutes after the peak for S electrode.

The SEM scanner 10 was also tested on the inner arm. A resistive pressure sensor (e.g. sensor 11 shown in FIG. 7) was also used to measure pressure applied on sensor to the arm. This way, constant pressure is applied across measurements. First, the dry inner arm was measured using the XS, S and M electrodes. Then, the same area was masked off with tape, and moisturizer lotion was applied for 30 minutes. Subsequent measurements were made on the same location after cleaning the surface.

Figure 12:
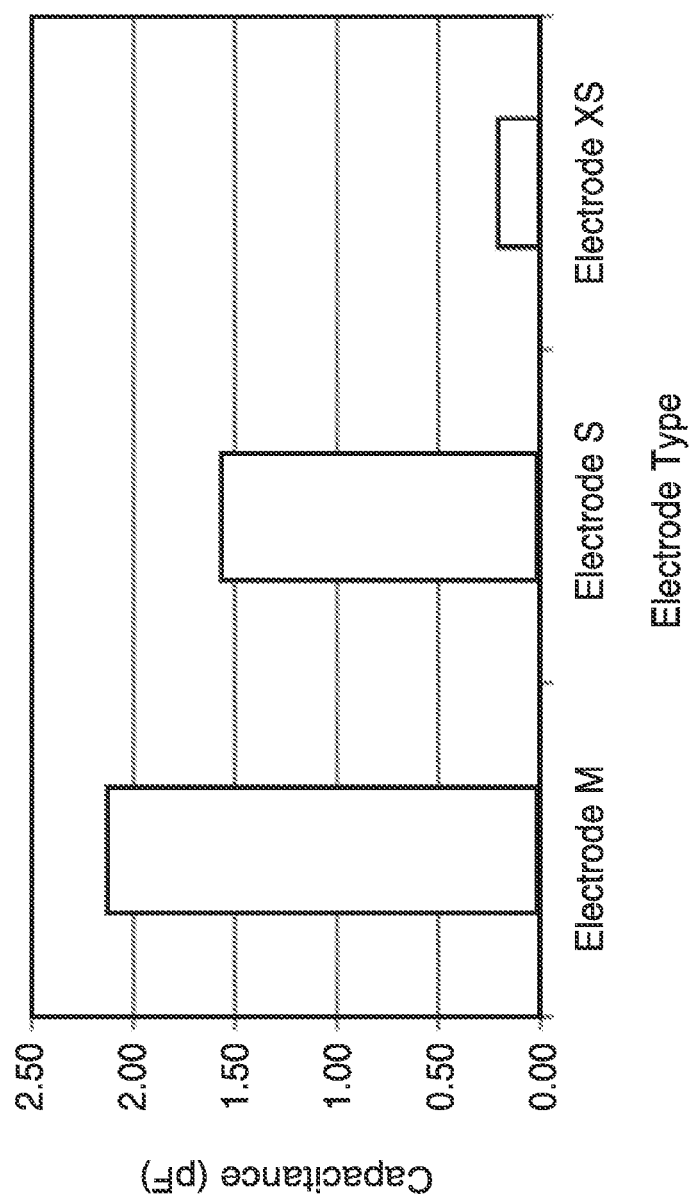
FIG. 12 is a graph of measured equivalent capacitance for dry volar arm for three different concentric sensor electrodes.

FIG. 12 is a graph of measured equivalent capacitance for dry Volar arm for three different sized (M, S, XS) concentric sensor electrodes before applying the commercial lotion moisturizer.

Figure 13:
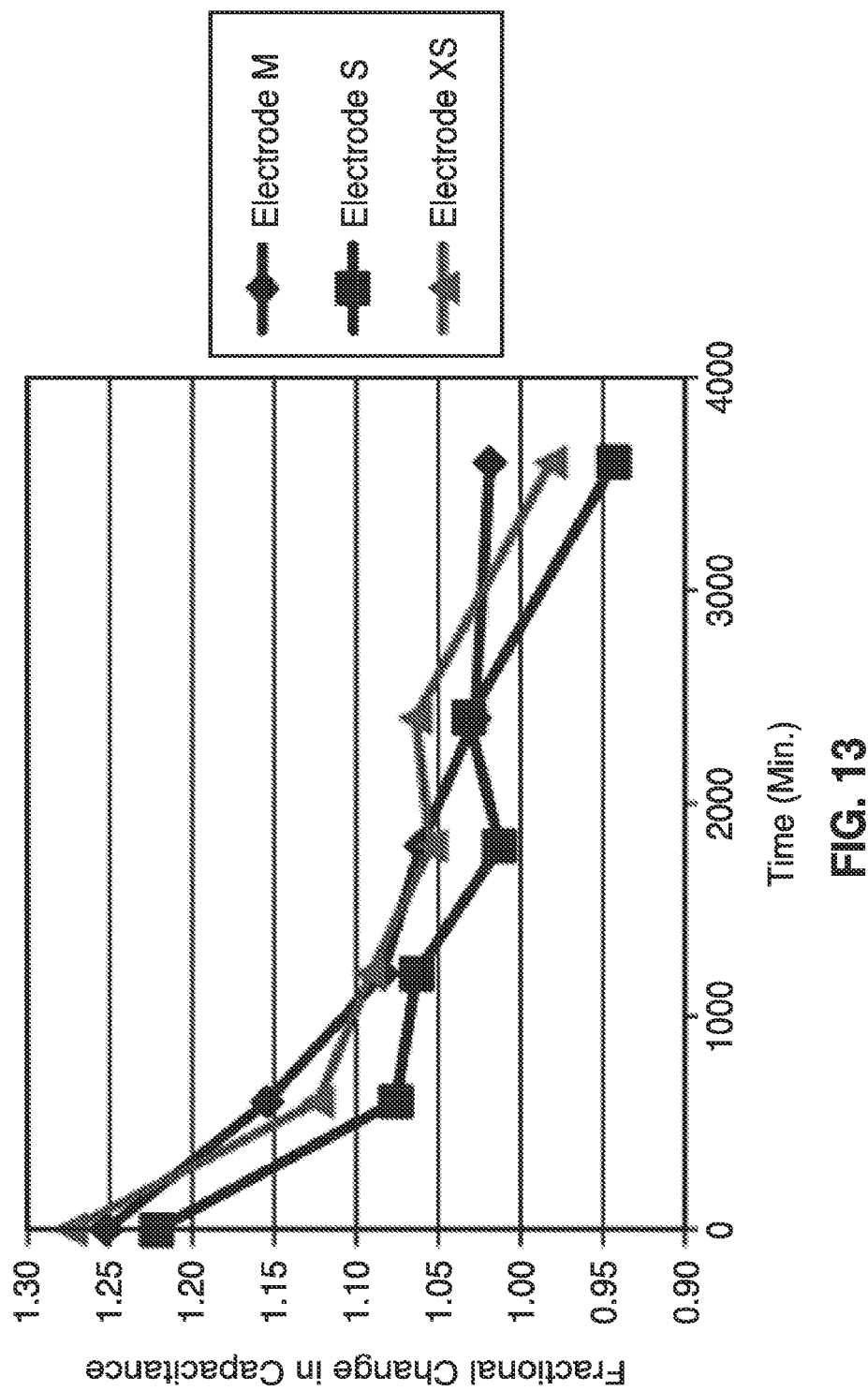
FIG. 13 is a plot of time dependent fractional change in capacitance relative to dry skin for three different concentric sensor electrodes (after 30 minutes of applying lotion).

FIG. 13 is a plot of time dependent fractional change in capacitance relative to dry skin for three different concentric sensor electrodes (after 30 minutes of applying lotion).

Figure 14:
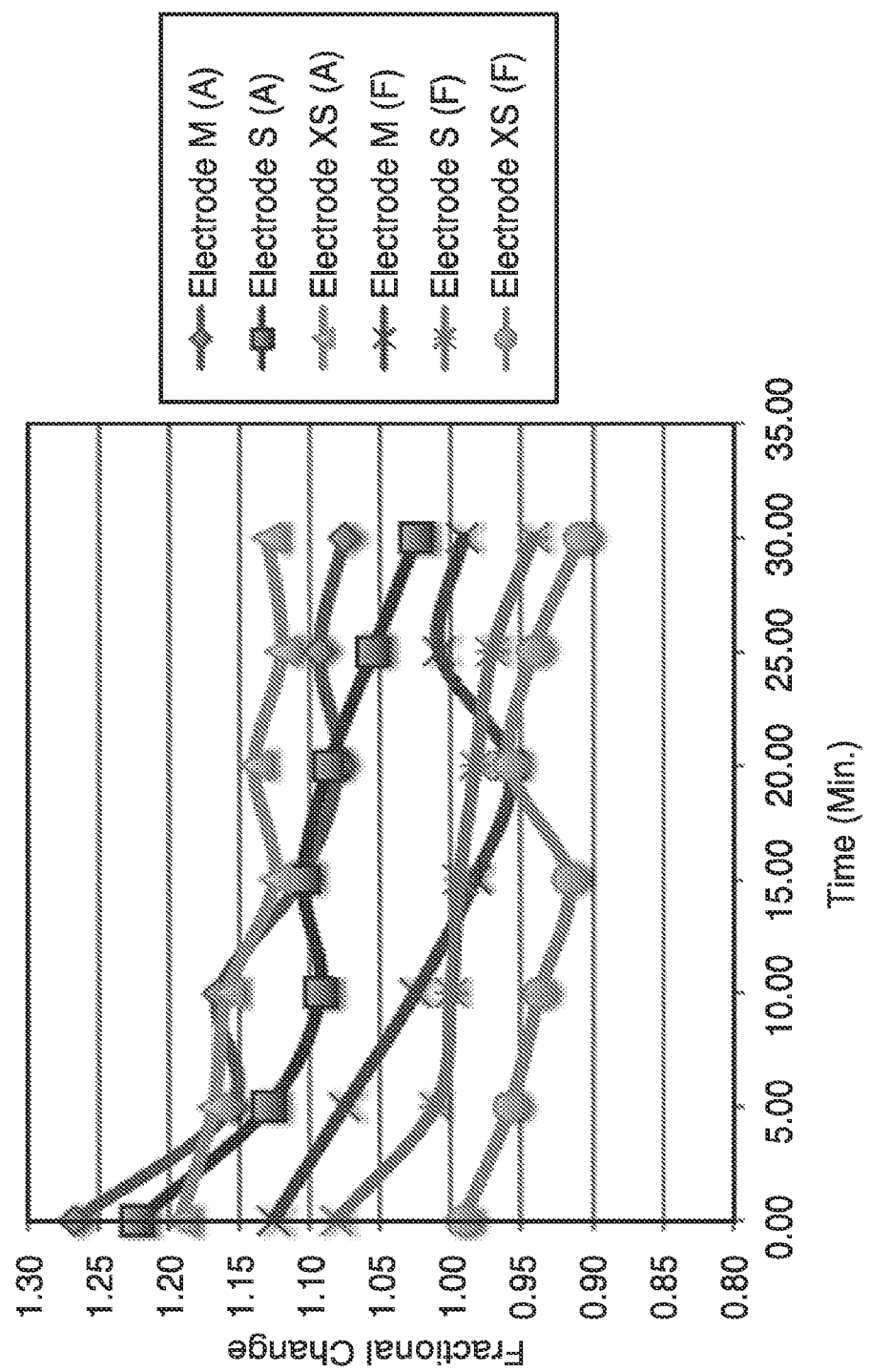
FIG. 14 is a plot of time dependent fractional change in capacitance relative to dry skin for three different concentric sensor electrodes (after 15 minutes of applying lotion).

FIG. 14 is a plot of time dependent fractional change in capacitance relative to dry skin for three different concentric sensor electrodes (after 15 minutes of applying lotion) on two subjects. This experiment was performed with faster sampling intervals and with lotion applied for 15 minutes only on forearms of two test subjects. Again, a resistive pressure sensor was used to measure pressure applied on sensor to the arm. This way, constant pressure is applied across measurements. First the dry inner arm was measured using the XS, S and M electrodes. Then the same area was masked off with tape, and lotion was applied for 15 minutes. Subsequent measurements were made on the same location every 5 minutes. Pressure was maintained at 50k Ohms, and the forearm was tested again. We noticed an interesting observation for the case "F" in comparison to case "A" and also compared to previous measurements. Case "F" took a shower right before running the measurements and hence as a result his skin was relatively saturated with moisture. As a result, we observed less degree of sensitivity to the applied deep moisturizer for case "F".

The experiment was performed again for case "F", with a time resolution of 3 minutes, knowing that the subject did not shower in the morning before the test. The lotion was applied to the inner forearm for 15 minutes. Pressure was maintained at 50k Ohms. The results confirm the sensitivity of the measurement to the residual skin moisture.

Figure 15:
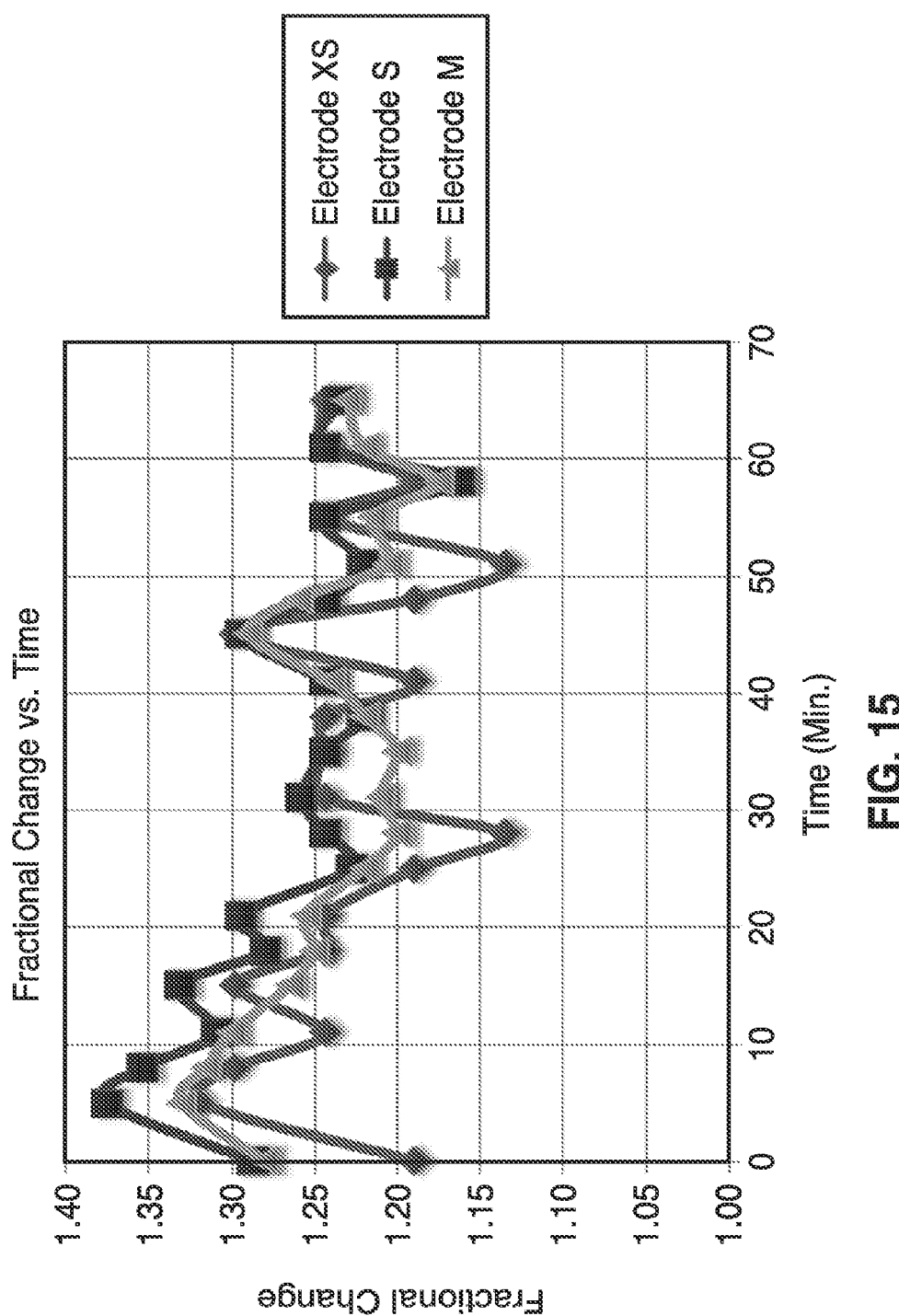
FIG. 15 is a plot of fractional change vs. time.

FIG. 15 is a plot of results for fractional change vs. time for M, S and XS electrodes.

Figure 16:
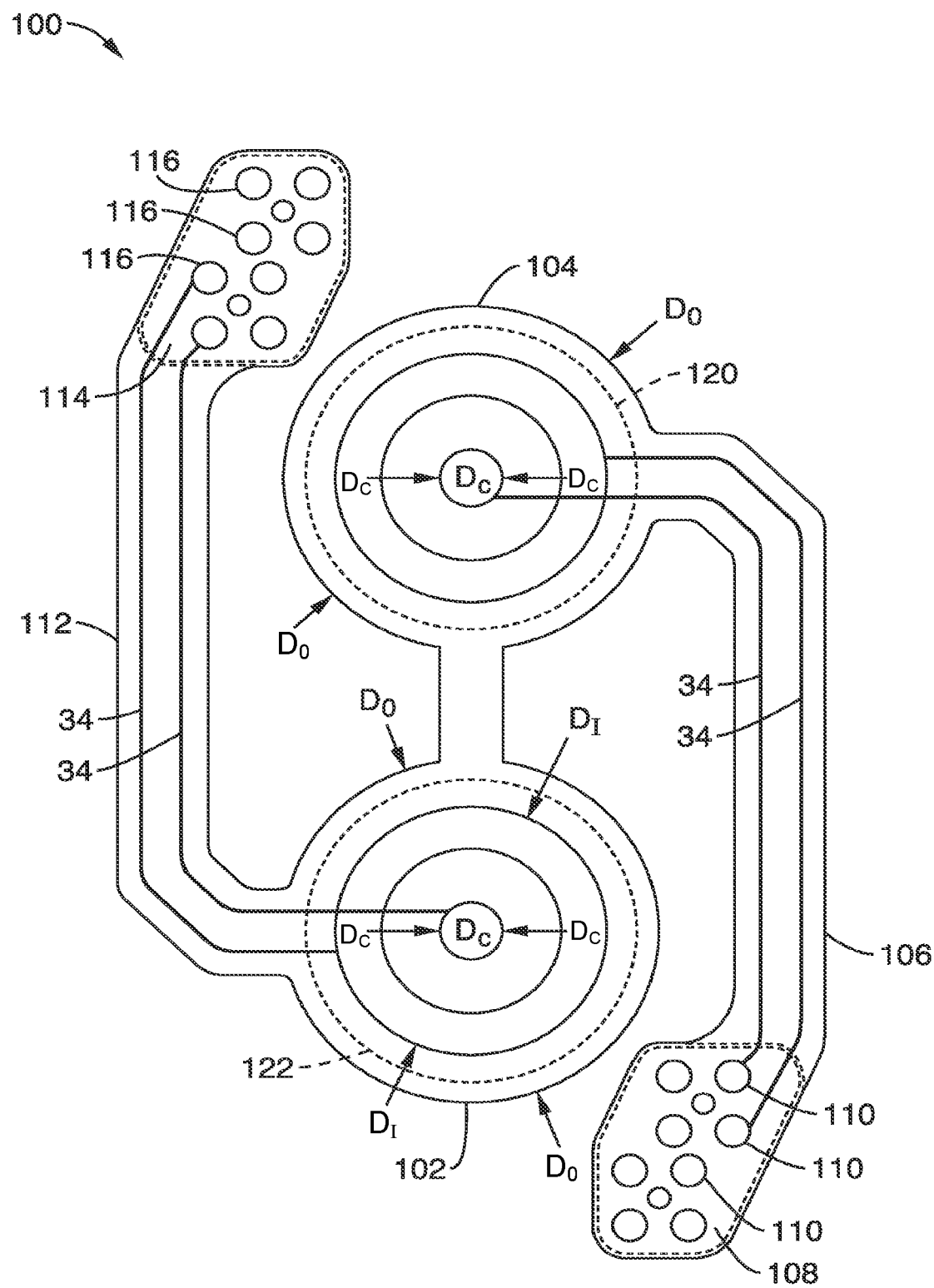
FIG. 16 shows a SEM scanner electrode system and electrode layering providing proper shielding from interference.

FIG. 16 shows a preferred embodiment of a layered SEM scanner electrode system 100 having a first electrode pad 102 and second electrode pad 104. Pad 104 is connected to lead line inputs 116 via wiring 34 along curved path 112. Pad 102 is connected to lead line inputs 110 via wiring 34 along curved path 106. A stiffener layer (e.g. layer 126 in FIG. 5) is provided directly under lead inputs 110 and 116 (see footprint 108 and 114 respectively) and under pads 102 and 104 (see footprint 122 and 120 respectively).

In this embodiment, the electrode size is approximately 2300 in width by 3910 mil in height.

Figure 17:
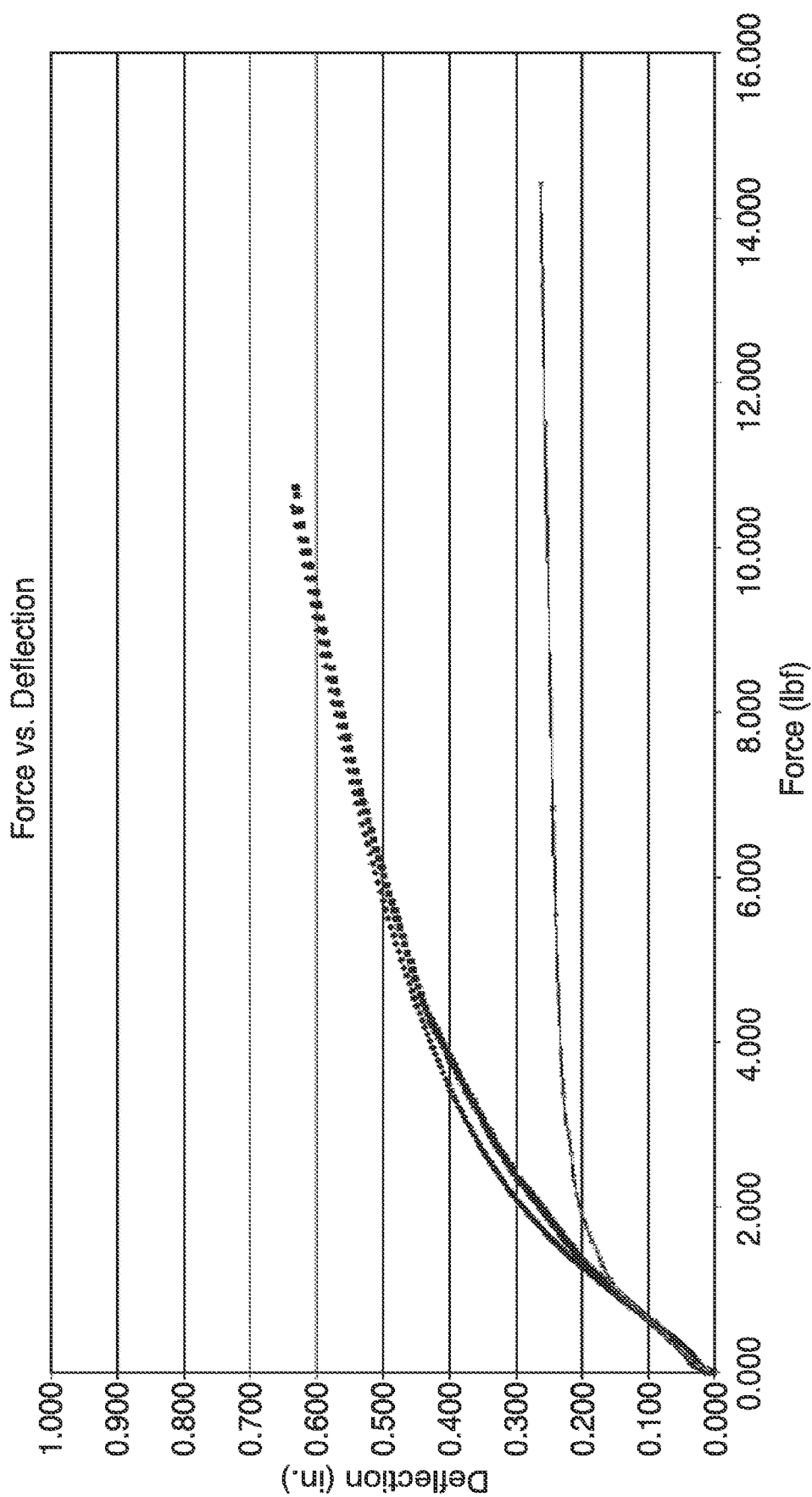
FIG. 17 shows an SEM scanner mechanical compliance for electrodes developed to enable probing of bony prominence.

FIG. 17 illustrates the SEM Scanner mechanical compliance (force-displacement relationship) for electrodes of system 100, developed to enable probing of bony prominence. The diamond symbols show the upper electrode 104 response, square symbols show the lower electrode 102 response.

The SEM scanner device 10 may also include other instruments, such as a camera (not shown), which can be used to take pictures of the wound, or develop a scanning system to scan barcodes as a login mechanism or an interrogator.

Patients using the SEM scanner device 10 may wear a bracelet (not shown) that contains data relating to their patient ID. This ID can be scanned by the camera embedded in the SEM scanner 10 to confirm correct patient ID correspondence. Alternatively, a separate RF scanner (not shown) may be used for interrogating the bracelet (in addition to the camera).

The SEM scanner device 10 is preferably ergonomically shaped to encourage correct placement of the device on desired body location.

The SEM Scanner device 10 of the present invention is capable of generating physical, absolute measurement values, and can produce measurements at multiple depths.

Figure 18:
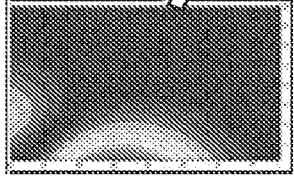
FIG. 18 is an overview of the wound registration method according to an embodiment of the description.

FIG. 18 shows the mapping function used to transform the target image.

In one embodiment of the description, wound images are obtained from a smart patch, which is able to retrieve multiple types of images from the same wound scan, including a moisture map and a pressure map of the bony prominence. This is summarized in FIG. 19.

Note the difference in our registration method from the previous work is that the two images can be significantly different from each other, due to the changes in wound healing. Additionally, we are aided from pressure readings obtained from the smart patch, which allow the improved registration of the more pertinent moisture maps. Bony prominence can be used in the feature detection phase.

Figure 19:
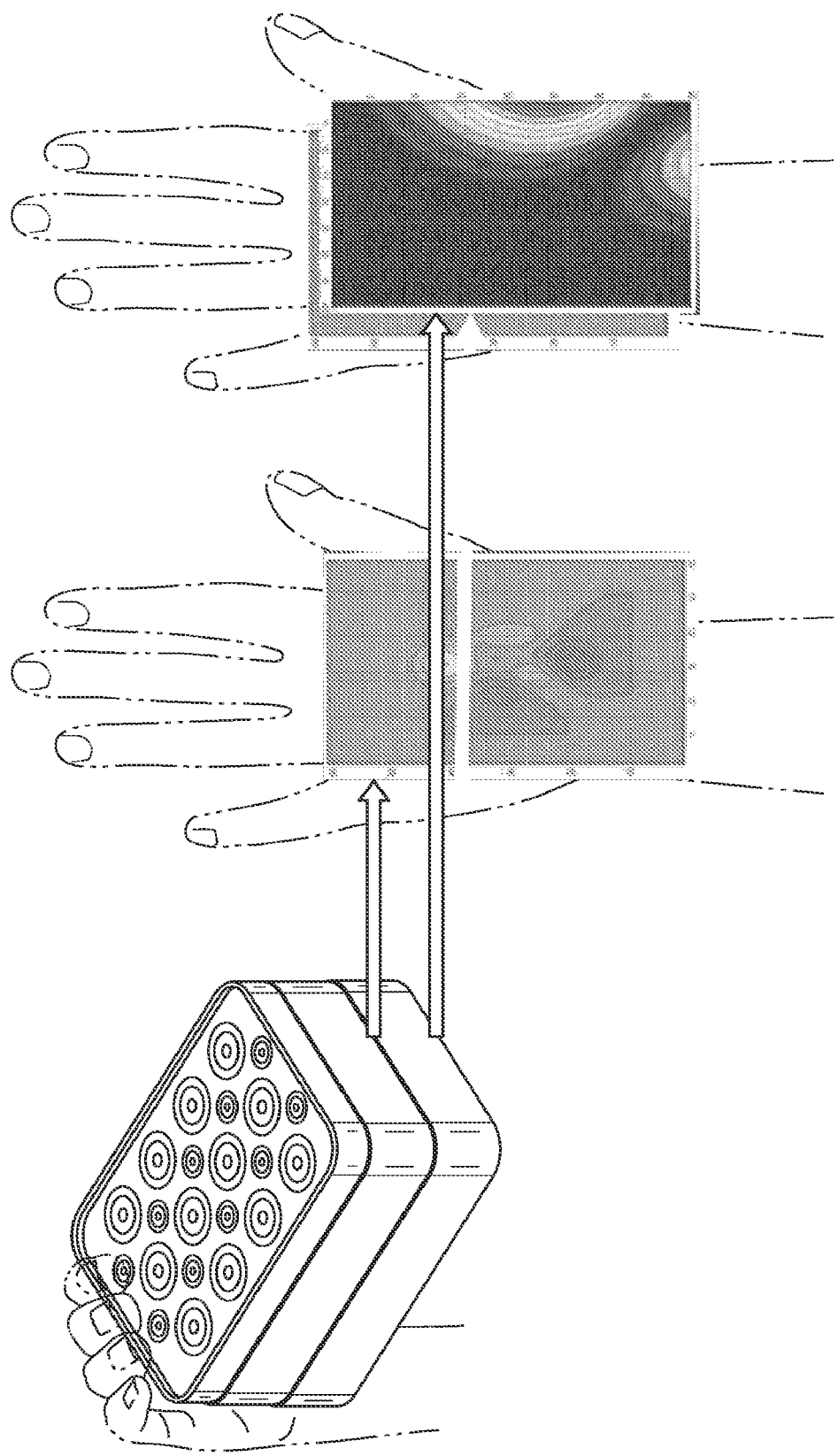
FIG. 19 illustrates pressure and moisture measurements obtained according to an embodiment of the description.

FIG. 19 demonstrates how both pressure and moisture measurements are obtained from the wound. This enables the registration of two different readings, obtained on two different days as shown in FIG. 20. The left column shows the reading, including pressure and moisture, from day 1 and the right column shows the reading from day 2. Note the images obtained are severely misaligned.

From the foregoing it will be appreciated that the present invention can be embodied in various ways, which include but are not limited to the following:

1. An apparatus for sensing sub-epidermal moisture from a location external to a patient's skin, comprising: a bipolar RF sensor embedded on a flexible substrate; a conformal pressure pad disposed adjacent and underneath the substrate; wherein the conformal pressure pad is configured to support the flexible substrate while allowing the flexible substrate to conform to a non-planar sensing surface of the patient's skin; and interface electronics coupled to the sensor; wherein said interface electronics is configured to control emission and reception of RF energy to interrogate the patient's skin.

2. The apparatus of embodiment 1, further comprising: an annular spacer adjacent and underneath the conformal pressure pad; wherein the annular spacer comprises a central opening configured to allow the conformal pressure pad to deflect freely into the central opening.

3. The apparatus of embodiment 1, further comprising: an array of bipolar RF sensors spaced across the flexible substrate; wherein each of the sensors is independently coupled to the interface electronics to independently interrogate the patient's skin.

4. The apparatus of embodiment 3: wherein each of the sensors is configured to measure an equivalent sub-epidermal capacitance of a target region of skin; said sub-epidermal capacitance corresponding to the moisture content of the target region of skin.

5. The apparatus of embodiment 4: wherein the array of sensors comprises a first sensor having a first contact area and a second sensor having a second contact area larger than the first sensor; wherein the first and second sensors interrogate the skin at different depths.

6. The apparatus of embodiment 4: wherein the substrate comprises a substrate assembly comprising a substrate layer; and wherein the sensor comprises a sensing pad having a first electrode embedded on a first side of the substrate and a second electrode embedded on a second side of the substrate.

7. The apparatus of embodiment 6, further comprising a biocompatible cover layer disposed over said first side of said substrate layer.

8. The apparatus of embodiment 6, further comprising a cover layer disposed under said second side of said substrate layer.

9. The apparatus of embodiment 6, further comprising a stiffener layer disposed under said second side of said substrate layer; wherein the stiffener layer comprises a footprint substantially similar to that of the sensor array.

10. The apparatus of embodiment 6: wherein said first electrode comprises an annular ring having an inner radius and an outer radius; wherein said second electrode comprises an outer radius having a smaller diameter than the inner radius of the first electrode; and wherein said second electrode is concentric with said first radius.

11. The apparatus of embodiment 1, wherein the interface electronics are configured to transmit data retrieved from said sensors.

12. The apparatus of embodiment 4, further comprising: a pressure sensor positioned in line with said RF sensor; said pressure sensor configured to measure an applied pressure of the substrate at a location on the patient's skin.

13. The apparatus of embodiment 1, wherein the flexible substrate comprises Kapton or Polyimide.

14. A scanner for sensing sub-epidermal moisture from a location external to a patient's skin, comprising: an array of bipolar RF sensors embedded on a flexible substrate; and a conformal pressure pad disposed adjacent and underneath the substrate; wherein the conformal pressure pad is configured to support the flexible substrate while allowing the flexible substrate to conform to a non-planar sensing surface of the patient's skin; wherein said sensor array is configured to emit and receive RF energy to interrogate the patient's skin; and wherein each of the sensors are independently are individually wired to independently interrogate the patient's skin.

15. The scanner of embodiment 14, further comprising: interface electronics coupled to the sensor; wherein said interface electronics is configured to control the emission and reception of RF energy.

16. The scanner of embodiment 14, further comprising: an annular spacer adjacent and underneath the conformal pressure pad; wherein the annular spacer comprises a central opening configured to allow the conformal pressure pad to deflect freely into the central opening.

17. The scanner of embodiment 14: wherein each of the sensors is configured to measure an equivalent sub-epidermal capacitance of a target region of skin; said sub-epidermal capacitance corresponding to the moisture content of the target region of skin.

18. The scanner of embodiment 14: wherein the array of sensors comprises a first sensor having a first contact area and a second sensor having a second contact area larger than the first sensor; and wherein the first and second sensors interrogate the skin at different depths.

19. The scanner of embodiment 14: wherein each sensor comprises a first electrode in the form of an annular ring having an inner radius and an outer radius and a second electrode comprising an outer radius having a smaller diameter than the first electrode; and wherein said second electrode is concentric with said first radius.

20. The scanner of embodiment 19: wherein the substrate comprises a substrate assembly comprising a substrate layer; and wherein the first electrode is embedded on a first side of the substrate and the second electrode embedded on a second side of the substrate.

21. The scanner of embodiment 20, further comprising: an upper biocompatible cover layer disposed over said first side of said substrate layer and a lower cover layer disposed under said second side of said substrate layer.

22. The scanner of embodiment 20, further comprising: a stiffener layer disposed under said second side of said substrate layer; wherein the stiffener layer comprises a footprint substantially similar to that of the sensor array.

23. The scanner of embodiment 14, further comprising: an array of pressure sensors positioned in line with said RF sensor; said pressure sensors are configured to measure an applied pressure of the substrate at corresponding locations on the patient's skin.

24. A method for monitoring the formation of pressure ulcers at a target location of a patient's skin, comprising: positioning a flexible substrate adjacent the target location of the patient's skin; the flexible substrate comprising one or more bipolar RF sensors; conforming the flexible substrate to the patient's skin at the target location; exciting the one or more bipolar RF sensor to emit RF energy into the patient's skin; and measuring the capacitance of the skin at the target location as an indicator of the Sub-Epidermal Moisture (SEM) at the target location.

25. The method of embodiment 24: wherein the one or more sensors comprise an array of sensors disposed across said substrate; and wherein the one or more sensors are individually controlled to independently excite the one or more sensors.

26. The method of embodiment 24, further comprising: measuring an applied pressure of the substrate at the target location on the patient's skin.

27. The method of embodiment 25, further comprising: measuring an applied pressure of the substrate on the patient's skin at each of the sensors in the array.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Symbol | XXS | XS | S | M | L |
|---|---|---|---|---|---|
| Contact Diameter (mm) | 5 | 10 | 20 | 23 | 55 |
| Approx Outer $D_o$ (mm) | 5 | 10 | 20 | 23 | 55 |
| Approx Middle $D_i$ (mm) | 4 | 6 | 10 | 15 | 40 |
| Approx Inner $D_c$ (mm) | 2 | 2 | 4 | 5 | 7 |

TABLE 2

Tabulated Normalized Responses of M, S, XS and XXS Electrodes

| Time | M | M Baseline | S | S Baseline | XS | XS Baseline | XXS | XXS Baseline |
|---|---|---|---|---|---|---|---|---|
| 0 | 2.32 | 2.04 | 1.89 | 1.5 | 0.261 | 0.24 | 1.12 | 1.04 |
| 5 | 2.32 | 2.04 | 1.9 | 1.5 | 0.256 | 0.24 | 1.1 | 1.04 |
| 10 | 2.38 | 2.04 | 1.92 | 1.5 | 0.259 | 0.24 | 1.07 | 1.04 |
| 15 | 2.4 | 2.04 | 1.99 | 1.5 | 0.255 | 0.24 | 1.06 | 1.04 |
| 20 | 2.39 | 2.04 | 1.93 | 1.5 | 0.248 | 0.24 | 1.05 | 1.04 |
| 25 | 2.25 | 2.04 | 1.92 | 1.5 | 0.25 | 0.24 | 1.04 | 1.04 |
| 30 | 2.21 | 2.04 | 1.88 | 1.5 | 0.248 | 0.24 | 1.04 | 1.04 |
| 35 | 2.18 | 2.04 | 1.86 | 1.5 | 0.245 | 0.24 | 1.04 | 1.04 |

What is claimed is:

1. An apparatus for in situ Sub-Epidermal Moisture (SEM) sensing of tissue, comprising:
a flexible substrate,
a first electrode and a second electrode forming a pair of bipolar electrodes, wherein the first electrode and the second electrode are both disposed on a common side of the flexible substrate;
an insulating cover layer coupled to the flexible substrate and configured to act as a barrier between the tissue being measured and the first electrode and the second electrode; and
an electronics package that is individually wired to each of the first electrode and the second electrode and configured to:
receive a pressure applied over the first and second electrodes, and
measure a capacitance between the first and second electrodes when the pressure is within a defined pressure range,
wherein the capacitance is an indicator of SEM.

2. The apparatus of claim 1, further comprising a pressure sensor coupled to the flexible substrate disposed in line with the first and second electrodes, wherein the pressure sensor is further electronically coupled to the electronics package and configured to provide a measure of the pressure to the electronics package.

3. The apparatus of claim 2, wherein the flexible substrate comprises a second side, and wherein the pressure sensor is coupled to the second side of the flexible substrate.

4. The apparatus of claim 1, further comprising a conformal pressure pad disposed in line with the first and second electrodes, wherein the conformal pressure pad is configured to support the flexible substrate while allowing the flexible substrate to conform to a non-planar sensing surface.

5. The apparatus of claim 1, wherein the second electrode is an annular electrode that is disposed around the first electrode.

6. The apparatus of claim 5, wherein the second electrode is concentrically disposed around the first electrode.

7. The apparatus of claim 5, wherein the first electrode and the second electrode are configured such that there is an annular gap between the first and second electrodes.

8. The apparatus of claim 7, wherein the annular gap is uniform.

9. The apparatus of claim 1, wherein the first and second electrodes are electrically insulated from each other.

10. The apparatus of claim 1, wherein the electronics package is configured to measure the capacitance between the first and second electrodes by emitting and receiving radio frequency (RF) energy.

11. The apparatus of claim 10, wherein the first and the second electrodes are coupled to the electronic package to form a bipolar RF sensor.

12. The apparatus of claim 1, wherein the electronics package is further configured to transfer measured data to a remote device.

13. The apparatus of claim 12, wherein the measured data is transferred via Bluetooth.

14. The apparatus of claim 12, wherein the remote device is a computer.

15. An apparatus for in situ Sub-Epidermal Moisture (SEM) sensing of tissue, comprising:
   a flexible substrate,
   a first electrode and a second electrode forming a pair of bipolar electrodes, wherein the first electrode and the second electrode are both disposed on a common side of the flexible substrate;
   an insulating cover layer coupled to the flexible substrate and configured to act as a barrier between the tissue being measured and the first electrode and the second electrode;
   an electronics package that is individually wired to each of the first electrode and the second electrode and configured to:
      receive a pressure applied over the first and second electrodes, and
      measure a capacitance between the first and second electrodes when the pressure is within a defined pressure range,
      wherein the capacitance is an indicator of SEM,
      wherein the electronics package is configured to measure the capacitance between the first and second electrodes by emitting and receiving radio frequency (RF) energy,
   wherein the first and the second electrodes are coupled to the electronic package to form a first bipolar RF sensor;
   a third electrode and a fourth electrode, both coupled to the electronics package to form a second bipolar RF sensor, wherein the first bipolar RF sensor has a first contact area and the second bipolar RF sensor has a second contact area larger than the first bipolar RF sensor, and wherein the first bipolar RF sensor and the second bipolar RF sensor interrogate the tissue at different depths.

16. An apparatus for in situ Sub-Epidermal Moisture (SEM) sensing of tissue, comprising:
   a flexible substrate,
   a plurality of electrodes comprising at least a first electrode and a second electrode forming a pair of bipolar electrodes, wherein the first electrode and the second electrode are both disposed on a common side of the flexible substrate;
   an insulating cover layer coupled to the flexible substrate and configured to act as a barrier between the tissue being measured and the first electrode and the second electrode;
   an electronics package that is individually wired to each of the first electrode and the second electrode and configured to:
      receive a pressure applied over the first and second electrodes, and
      measure a capacitance between the first and second electrodes when the pressure is within a defined pressure range,
      wherein the capacitance is an indicator of SEM,
      wherein the electronics package is configured to measure the capacitance between the first and second electrodes by emitting and receiving radio frequency (RF) energy,
   wherein the plurality of electrodes coupled to the electronics package to form a plurality of bipolar RF sensors, and wherein the electronics package is further configured to measure a capacitance associated with each of the plurality of bipolar RF sensors when the pressure is within the defined pressure range to generate an SEM image of the tissue.

* * * * *